(12) United States Patent
Ashby et al.

(10) Patent No.: US 6,984,219 B2
(45) Date of Patent: Jan. 10, 2006

(54) DEPTH AND PUNCTURE CONTROL FOR BLOOD VESSEL HEMOSTASIS SYSTEM

(76) Inventors: Mark Ashby, 30012 Bello Pl., Laguna Niguel, CA (US) 92677; Andrew Cragg, 4502 Edina Blvd., Edina, MN (US) 55424; Luis Urquidi, 22146 Caminito Laureles, Laguna Hills, CA (US) 92653; Eduardo Chi-Sing, 5 Terraza Del Mar, Dana Point, CA (US) 92629; Eric Lee, 18 Wintersweet Way, Irvine, CA (US) 92612

(*) Notice: Subject to any disclaimer, the term of this patent is extended or adjusted under 35 U.S.C. 154(b) by 471 days.

(21) Appl. No.: 09/859,682

(22) Filed: May 18, 2001

(65) Prior Publication Data

US 2002/0062104 A1 May 23, 2002

Related U.S. Application Data

(60) Provisional application No. 60/156,007, filed on Sep. 23, 1999.

(51) Int. Cl.
*A61F 13/36* (2006.01)

(52) U.S. Cl. .......................................... 604/15
(58) Field of Classification Search ............... 604/27, 604/15, 60; 239/16, 20, 24, 33; 606/213, 606/191
See application file for complete search history.

(56) References Cited

U.S. PATENT DOCUMENTS

| | | | |
|---|---|---|---|
| 581,235 A | 4/1897 | Kenyon | |
| 1,578,517 A | 3/1926 | Hein | |
| 2,086,580 A | 7/1937 | Shirley | |
| 2,370,319 A | 2/1945 | Lippincott | |
| 2,465,357 A | 3/1949 | Correll | |

(Continued)

FOREIGN PATENT DOCUMENTS

| | | |
|---|---|---|
| EP | 0032826 | 7/1981 |
| EP | 0476178 | 3/1992 |
| EP | 0482350 | 4/1992 |
| EP | 0557963 | 2/1993 |
| EP | 0637431 | 11/1994 |

(Continued)

OTHER PUBLICATIONS

Allison, D., et al., "Percutaneous liver biopsy and track embolization with steel coils", Radiology, vol. 169, pp. 261–263, (1998).

J. Bryne Review Article: Endovascular treatments for intracranial anuerysms, 1996 The British journal of radiology; 98, 891–899.

Chuang, V., et al., "Sheath needle for liver biopsy in high–risk patience", Radiology, vol. 166, pp. 261–262 (1988).

John T. Correll, et al., A new Physiology absorbable sponge.

John T. Correll, et al. Biologic investigation of new absorbable sponge; p. 585.

Fandrich, C., et al., "Small guage gelfoam plug liver biopsy in high risk patients", Australian Radiology, vol. 40, pp. 230–234 (1996).

(Continued)

*Primary Examiner*—Ismael Izaguirre
(74) *Attorney, Agent, or Firm*—Marshall, Gerstein & Borun LLP

(57) ABSTRACT

A depth and puncture control system for a blood vessel hemostasis system includes a blood vessel puncture control tip which, when positioned in the lumen of a blood vessel, can inhibit the flow of blood out of the puncture site. When used together with a pledget delivery cannula and a pledget pusher, the control tip and the delivery catheter can both inhibit blood loss out the puncture site and inhibit the introduction of pledget material and tissue fragments into the blood vessel. The system also includes a handle which releasably connects together the control tip, pusher, and delivery cannula to permit limited longitudinal motion between the control tip and the delivery cannula, and between the pusher and the delivery cannula.

33 Claims, 29 Drawing Sheets

U.S. PATENT DOCUMENTS

| | | | |
|---|---|---|---|
| 2,492,458 A | 12/1949 | Bering, Jr. | |
| 2,507,244 A | 5/1950 | Correll | |
| 2,558,395 A | 6/1951 | Studer | |
| 2,597,011 A | 5/1952 | MacMasters et al. | |
| 2,680,442 A | 6/1954 | Linzmayer | |
| 2,761,446 A | 9/1956 | Reed | |
| 2,814,294 A | 11/1957 | Figge | |
| 2,824,092 A | 2/1958 | Thompson | |
| 2,874,776 A | 2/1959 | Hooe | |
| 2,899,362 A | 8/1959 | Sieger, Jr. et al. | |
| 2,997,195 A * | 8/1961 | Yuen | 215/388 |
| 3,157,524 A | 11/1964 | Artandi | |
| 3,358,689 A | 12/1967 | Higgins | |
| 3,411,505 A | 11/1968 | Nobis | |
| 3,703,174 A | 11/1972 | Smith | |
| 3,724,465 A | 4/1973 | Duchane | |
| 3,736,939 A | 6/1973 | Taylor | |
| 4,000,741 A | 1/1977 | Binard et al. | |
| 4,098,728 A | 7/1978 | Rosenblatt | |
| 4,211,323 A | 7/1980 | Olsen | |
| 4,218,155 A | 8/1980 | Weidner | |
| 4,219,026 A | 8/1980 | Layton | |
| 4,224,945 A | 9/1980 | Cohen | |
| 4,238,480 A | 12/1980 | Sawyer | |
| 4,292,972 A | 10/1981 | Pawelchak | |
| 4,323,072 A | 4/1982 | Rosenbluth et al. | |
| 4,340,066 A | 7/1982 | Shah | |
| 4,390,018 A | 6/1983 | Zuloowski | |
| 4,404,970 A | 9/1983 | Sawyer | |
| 4,405,314 A | 9/1983 | Cope | |
| 4,515,637 A | 5/1985 | Cioca | |
| 4,587,969 A | 5/1986 | Gillis | |
| 4,588,395 A | 5/1986 | Lemelson | |
| 4,591,094 A * | 5/1986 | Morris | 239/17 |
| 4,619,261 A | 10/1986 | Guerriero | |
| 4,619,913 A | 10/1986 | Luck et al. | |
| 4,644,649 A | 2/1987 | Seaman et al. | |
| 4,645,488 A | 2/1987 | Matukas | |
| 4,699,616 A | 10/1987 | Norwak | |
| 4,708,718 A | 11/1987 | Daniels | |
| 4,744,364 A | 5/1988 | Kensey | |
| 4,790,819 A | 12/1988 | Li et al. | |
| 4,829,994 A | 5/1989 | Kurth | |
| 4,832,688 A | 5/1989 | Sagae et al. | |
| 4,839,204 A | 6/1989 | Yoshino | |
| 4,850,960 A | 7/1989 | Grayzel | |
| 4,852,568 A | 8/1989 | Kensey | |
| 4,869,143 A | 9/1989 | Merrick | |
| 4,890,612 A | 1/1990 | Kensey | |
| 4,900,303 A | 2/1990 | Lemelson | |
| 4,929,246 A | 5/1990 | Sinofaky | |
| 4,936,835 A | 6/1990 | Haaga | |
| 4,950,234 A | 8/1990 | Fujioka et al. | |
| 5,007,895 A | 4/1991 | Burnett | |
| 5,021,059 A | 6/1991 | Kensey et al. | |
| 5,049,138 A | 9/1991 | Chevalier et al. | |
| 5,053,046 A | 10/1991 | Janese | |
| 5,061,274 A | 10/1991 | Kensey | |
| 5,080,655 A | 1/1992 | Haaga | |
| 5,106,376 A | 4/1992 | Mononen et al. | |
| 5,108,421 A | 4/1992 | Fowler | |
| 5,129,889 A | 7/1992 | Hahn | |
| 5,160,323 A | 11/1992 | Andrew | |
| 5,163,904 A | 11/1992 | Lampropoulous et al. | |
| 5,167,624 A | 12/1992 | Butler et al. | |
| 5,192,290 A | 3/1993 | Hilal | |
| 5,192,300 A | 3/1993 | Fowler | |
| 5,192,301 A | 3/1993 | Kamiya et al. | |
| 5,195,988 A | 3/1993 | Haaga | |
| 5,219,899 A | 6/1993 | Panster et al. | |
| 5,220,926 A | 6/1993 | Jones | |
| 5,221,259 A | 6/1993 | Weldon et al. | |
| 5,232,453 A | 8/1993 | Plass et al. | |
| 5,242,683 A | 9/1993 | Klaveness | |
| 5,254,105 A | 10/1993 | Haaga | |
| 5,275,616 A | 1/1994 | Fowler | |
| 5,282,827 A | 2/1994 | Kensey et al. | |
| 5,299,581 A | 4/1994 | Donnell et al. | |
| 5,310,407 A | 5/1994 | Casale | |
| 5,320,639 A | 6/1994 | Rudnick | |
| 5,322,515 A | 6/1994 | Karas et al. | |
| 5,325,857 A | 7/1994 | Nabai et al. | |
| 5,334,216 A | 8/1994 | Vidal et al. | |
| 5,342,388 A | 8/1994 | Toller | |
| 5,350,399 A | 9/1994 | Erlebacher et al. | |
| 5,352,211 A | 10/1994 | Merskelly | |
| 5,366,480 A | 11/1994 | Corriveau et al. | |
| 5,370,656 A | 12/1994 | Shevel | |
| 5,383,896 A | 1/1995 | Gershony et al. | |
| 5,383,899 A | 1/1995 | Hammersiag | |
| 5,385,550 A | 1/1995 | Su et al. | |
| 5,388,588 A | 2/1995 | Nabai et al. | |
| 5,391,183 A | 2/1995 | Janzen et al. | |
| 5,399,361 A | 3/1995 | Song et al. | |
| 5,417,699 A | 5/1995 | Klein | |
| 5,419,765 A | 5/1995 | Weldon et al. | |
| 5,431,639 A | 7/1995 | Shaw | |
| 5,437,292 A | 8/1995 | Kipshidze | |
| 5,437,631 A | 8/1995 | Janzen | |
| 5,443,481 A | 8/1995 | Lee | |
| 5,447,502 A | 9/1995 | Haaga | |
| 5,458,570 A | 10/1995 | May, Jr. | |
| 5,462,194 A * | 10/1995 | Barnwell | 220/709 |
| 5,467,780 A | 11/1995 | Nabai et al. | |
| 5,478,352 A | 12/1995 | Fowler | |
| 5,479,936 A | 1/1996 | Nabai et al. | |
| 5,486,195 A | 1/1996 | Myers | |
| 5,490,736 A | 2/1996 | Haber | |
| 5,507,279 A | 4/1996 | Fortune | |
| 5,522,840 A | 6/1996 | Krajicek | |
| 5,522,850 A | 6/1996 | Yomtov et al. | |
| 5,526,822 A | 6/1996 | Burbank et al. | |
| 5,527,332 A | 6/1996 | Clement | |
| 5,529,577 A | 6/1996 | Hammershiag | |
| 5,540,715 A | 7/1996 | Katseros et al. | |
| 5,542,914 A | 8/1996 | Van Iten | |
| 5,545,175 A | 8/1996 | Abidin et al. | |
| 5,545,178 A | 8/1996 | Kensey et al. | |
| 5,554,108 A | 9/1996 | Browning et al. | |
| 5,558,853 A | 9/1996 | Quay | |
| 5,571,168 A | 11/1996 | Toro | |
| 5,591,204 A | 1/1997 | Janzen et al. | |
| 5,591,205 A | 1/1997 | Fowler | |
| 5,601,207 A * | 2/1997 | Paczonay | 220/703 |
| 5,601,601 A | 2/1997 | Tal et al. | |
| 5,601,602 A | 2/1997 | Fowler | |
| 5,601,603 A | 2/1997 | Illi | |
| 5,620,461 A | 4/1997 | Muijs Van De Moer | |
| 5,645,566 A | 7/1997 | Brennenman et al. | |
| 5,645,849 A | 7/1997 | Pruss et al. | |
| 5,649,547 A | 7/1997 | Ritchart et al. | |
| 5,653,730 A | 8/1997 | Hammersiag | |
| 5,665,107 A | 9/1997 | Hammersiag | |
| 5,674,346 A | 10/1997 | Kundel | |
| 5,676,689 A | 10/1997 | Kensey | |
| 5,681,279 A | 10/1997 | Roper et al. | |
| 5,707,393 A | 1/1998 | Kensey et al. | |
| 5,716,375 A | 2/1998 | Fowler | |
| 5,725,498 A | 3/1998 | Janzen et al. | |
| 5,741,223 A | 4/1998 | Janzen et al. | |
| 5,769,086 A | 6/1998 | Ritchart et al. | |

| | | | |
|---|---|---|---|
| 5,775,333 | A | 7/1998 | Burbank et al. |
| 5,782,861 | A | 7/1998 | Cragg et al. |
| 5,800,389 | A | 9/1998 | Burney et al. |
| 5,810,806 | A | 9/1998 | Ritchart et al. |
| 5,827,218 | A * | 10/1998 | Nguyen et al. ............... 604/30 |
| 5,830,130 | A | 11/1998 | Janzen et al. |
| 5,858,008 | A | 1/1999 | Capaccio |
| 5,868,762 | A | 2/1999 | Cragg et al. |
| 5,902,310 | A | 5/1999 | Foerster et al. |
| 5,931,165 | A | 8/1999 | Reich et al. |
| 5,984,950 | A | 11/1999 | Cragg et al. |
| 6,007,563 | A | 12/1999 | Nash et al. |
| 6,027,471 | A | 2/2000 | Fallon et al. |
| 6,027,482 | A | 2/2000 | Imbert |
| 6,033,427 | A | 3/2000 | Lee |
| 6,056,768 | A | 5/2000 | Cates et al. |
| 6,063,061 | A | 5/2000 | Wallace et al. |
| 6,066,325 | A | 5/2000 | Wallace et al. |
| 6,071,300 | A | 6/2000 | Brenneman et al. |
| 6,071,301 | A | 6/2000 | Cragg et al. |
| 6,086,607 | A | 7/2000 | Cragg et al. |
| 6,090,130 | A | 7/2000 | Nash et al. |
| 6,126,675 | A | 10/2000 | Shchervinsky et al. |
| 6,161,034 | A | 12/2000 | Burbank et al. |
| 6,162,192 | A * | 12/2000 | Cragg et al. ................ 604/15 |
| 6,183,497 | B1 | 2/2001 | Sing et al. |
| 6,197,327 | B1 | 3/2001 | Harrison et al. |
| 6,200,328 | B1 | 3/2001 | Cragg et al. |
| 6,315,753 | B1 * | 11/2001 | Cragg et al. ................ 604/15 |
| 6,371,974 | B1 | 4/2002 | Brenneman et al. |
| 6,440,151 | B1 | 8/2002 | Cragg et al. |
| 6,440,153 | B2 | 8/2002 | Cragg et al. |
| 6,447,534 | B2 | 9/2002 | Cragg et al. |
| 6,503,222 | B2 * | 1/2003 | Lo ............................. 604/77 |
| 6,527,734 | B2 | 3/2003 | Cragg et al. |
| 6,540,735 | B1 * | 4/2003 | Ashby et al. ............... 604/523 |
| 6,544,236 | B1 | 4/2003 | Cragg et al. |
| 6,547,806 | B1 | 4/2003 | Ding |
| 6,585,680 | B2 * | 7/2003 | Bugge ......................... 604/27 |
| 6,610,026 | B2 | 8/2003 | Cragg et al. |
| 2002/0002889 | A1 | 1/2002 | Ashby et al. |
| 2002/0016612 | A1 | 2/2002 | Ashby et al. |
| 2002/0038133 | A1 | 3/2002 | Sing et al. |
| 2002/0042378 | A1 | 4/2002 | Reich et al. |
| 2002/0062104 | A1 | 5/2002 | Ashby et al. |
| 2002/0156495 | A1 | 10/2002 | Brenneman et al. |
| 2003/0028140 | A1 | 2/2003 | Greff et al. |
| 2003/0088269 | A1 | 5/2003 | Ashby |
| 2003/0088271 | A1 | 5/2003 | Cragg et al. |
| 2003/0120258 | A1 | 6/2003 | Ashby et al. |
| 2003/0135237 | A1 | 7/2003 | Cragg et al. |
| 2004/0019328 | A1 | 1/2004 | Sing et al. |
| 2004/0019330 | A1 | 1/2004 | Ashby |

FOREIGN PATENT DOCUMENTS

| | | |
|---|---|---|
| EP | 0637432 B1 | 10/1997 |
| FR | 2641692 | 7/1990 |
| GB | 1509023 | 4/1978 |
| GB | 1569660 | 6/1980 |
| RU | 1088709 A | 4/1984 |
| SU | 782814 | 11/1980 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 97/09934 | 3/1997 |
| WO | WO 98/06346 | 2/1998 |
| WO | WO 99/66834 | 12/1999 |

OTHER PUBLICATIONS

Foran, JPM, et al. "Early mobilisation after percutaneous cardiac catheterisation using collagen plug (vasoseal) maemostatis" BRHeart, vol. 69, pp. 424–429 (1993).

Gibbs, JSR, "Femoral arterial hemostasis" J. Interventional card, vol. 5, pp. 85–88 (1992).

Journal of interventional cardiology vol. 5 No. 2 Jun.

Kassell, et al. Size of Intracanial aneurysm; vol. 12, No. 3, (1983).

Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685–1692 (1995).

Kussmaul, WG, "Rapid arterial hemostasis", J. Am. Coll. Card., vol. 25, pp. 1685–1692 (1995).

Pharmacia & Upjohn manufacturer brochure gelfoam sterile sponge, sterile powder and sterile film, pp 1–34 (May 1997).

Pharmacia & Upjohn manufacturer brochure "gelfoam sterile powder", (Feb. 1996).

Pharmacia & Upjohn manufacturer brochure, "gelfoam sterile powder" (Mar. 1996).

Pharmacia & Upjohn manufacturer brochure (Sep. 1996).

Pharmacia & Upjohn manufacturer specification, "Gelfoam sterile sponge, sterile powder and sterile film" pp. 1–23 (Nov. 1996).

Riley, SA, Percutaneous liver biopsy with plugging of needle track: a safe method for use in patients with impaired coagulation, The lancet, p. 436 (1964).

Sanborn, T. Multicenter randomized trial comparing perutaneous collagen hemostasis device with conventional manual compression after diagnostic angiography and angioplasty, J. Am. Coll. Card., vol. 22, pp. 1273–1279, (1993).

Schievink, et al., The new england journal of medicaine; review articles; intracanial aneurysms; Jan. 2, 1997.

Scharader, R. "Collagen appl.", Catheterization & cardiovascular diagnosis (1992) pp. 298–302.

Silber, S., "Rapid hemostasis of arterial puncture sites with collagen in patients undergoing diagnostic interventional cardiac catherterization", clinical cardiology, vol. 20, pp. 981–992, (1997).

Smith, T., "Percutaneous transhepatic liver biopsy with tract embolization", Radiology, vol. 198, pp. 769–774 (1996).

Szikora, et al. Combined Use of stents and cells to treat experimental wide–necked carotid aneuryms: Preliminary results; AJNR AM newradiol 15: 1091–1102, Jun. 94.

Szikora, et al. Endovascular treatment of experimental anuerysms with liquid polymers: vol. 38, No. 2, Feb. 96.

Turjman, et al. Combined stent implantation & endosacular coil placement for treatment of experimental wide–necked aneurysms:AJNRAM J. Neuroradio 15: 1087–1090 Jun. 94.

Yoshimoto, et al cerebral anuerysms unrelated to arterial bifurcations; Acta neurochir (Wien) (96) 138: 958–964.

Zins, M., "US–guided percutaneous liver biopsy with plugging of the needle track" radiology, vol. 187, pp. 841–843, (1992).

Ashby, Mark et al; U.S. Appl. No. 10/287,922; filed Nov. 4, 2002; entitled: Apparatus And Method For Inhibiting Blood Loss.

Ashby, Mark et al; U.S. Appl. No. 10/069,107; filed Dec. 16, 2002; entitled: Device And Method For Determining A Depth Of An Incision.

Ashby, Mark et al; U.S. Appl. No. 10/278,710; filed Oct. 22, 2002; entitled: System and Method for Faciliating Hemostasis of Blood Vessel Punctures With Absorbable Sponge.

Ashby, Mark et al; U.S. Appl. No. 10/334,770; filed Dec. 31, 2002; entitled: Improved System and Method for Faciliating Hemostasis with Absorbable Sponge.

Ashby, Mark et al; U.S. Appl. No. 10/421,680; filed Apr. 22, 2003; entitled: Puncture Closure System With Pin And Pull Technique.

Ashby, Mark et al; U.S. Appl. No. 10/462,065; filed Jun. 12, 2003; entitled: Enhanced Bleed Back System.

Ashby, Mark et al, U.S. Appl. No. 10/462,064; filed Jun. 12, 2003; entitled: Release Mechanism.

Ashby, Mark et al; U.S. Appl. No. 10/461,587; filed Jun. 12, 2003; entitled: Dissolvable Closure Device.

Ashby, Mark et al; U.S. Appl. No. 10/461,035; filed Jun. 13, 2003; entitled: System And Method For Delivering Hemostasis Promoting Material To A Blood Vessel Puncture Site.

Ashby, Mark et al; U.S. Appl. No. 10/461,006; filed Jun. 13, 2003; entitled: System and Method for Delivering Hemostasis Promoting Material to a Blood Vessel Puncture with a Staging Tube.

Ashby, Mark et al; U.S. Appl. No. 10/460,859; filed Jun. 12, 2003; entitled: Hemostatic Device Including a Capsule.

Ashby, Mark et al; U.S. Appl. No. 10/732,441; filed Dec. 9, 2003; entitled: Pledget–Handling System and Method for Delivering Hemostasis Promoting Material to a Blood Vessel Puncture Site By Fluid Pressure.

Ashby, Mark et al; U.S. Appl. No. 10/754,824; filed Jan. 9, 2004; entitled: Sheath–Mounted Arterial Plug Delivery Device.

Allison, D., et al., "Purcutaneous Liver Biopsy and Track Embolization with Steel Coils" Radiology 1998; 169:169–263, vol. 169, No. 1.

Berman, et al "Guided Direct Antegrade Puncture of the Superficial Femoral Artery" AJR 147:632–634, 9/86 0361–803X/86/1473–0632 © American Roentgen Ray Society.

Berman et al "Modification of the Cope Drainage Catheter to Facilitate Placement" AJR 146:169–170, 1/86 0361–803X/86/1461–0169 © American Ray Society.

Byrne, J., Review Article: "Endovascular treatments for intracranial aneurysms" 1996 The British Journal of Radiology, 69, 891–899.

Chuang, V., et al "Sheath Needle for Liver Biopsy in High–Risk Patients", Radiology 1988; 166:261–262.

Correll J., et al "Certain Properties of a New Physiology Absorbable Sponge", Research Laboratories of the Upjohn Company, Kalamasoo, Mich. 14908 P, pp. 233–235.

Correl J., et al "Biologic Investigation of a New Absorbable Sponge", pp. 585–589.

Di Seni, Ricardo, et al, Part 1, Ebolotherapy: "Agents, Equipment, and Techniques," Vascular Embolotherapy, vol. 4, pp. 29 & 33.

Fandrich, C., et al "Small gauge gelfoam plug liver biopsy in high risk patients: Safety and diagnostic value", Australian Radiology, 1996, 40, 230–234.

Saddekni, MD et al "Antegrade Catheterization of the Superficial Femoral Artery" Radiology 1985 157:561–532.

Scharader R., "Collagen Application for Sealing of Arterial Puncture Sites in Comparison to Pressure Dressing: A Randomized Trial" Catheterization and Cardiovascular Diagnosis 27: 298–302.

Vogelzang, R., "A Modified Cope Introducing Dilator to Allow Straight Guide Wire Introduction", AJR 146:381–382, 2/86 0361–803X/86/1462–0381 © American Roentgen Ray Society.

Pharmacia & Upjohn manufacture brochure "gelfoam sterile powder" (Feb. 1996).

Pharmacia & Upjohn manufacture brochure "gelfoam sterile powder" (Mar. 1996).

* cited by examiner

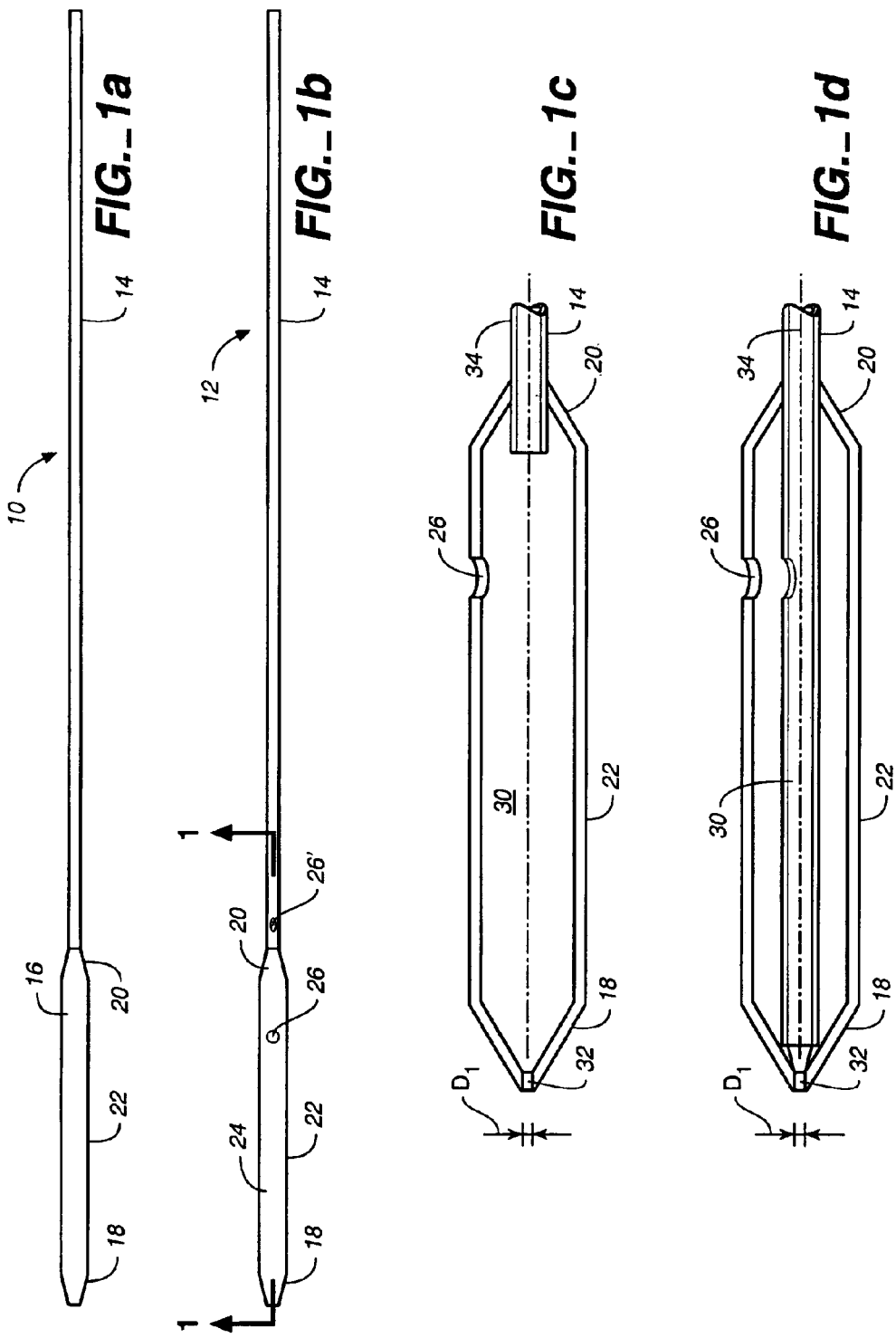

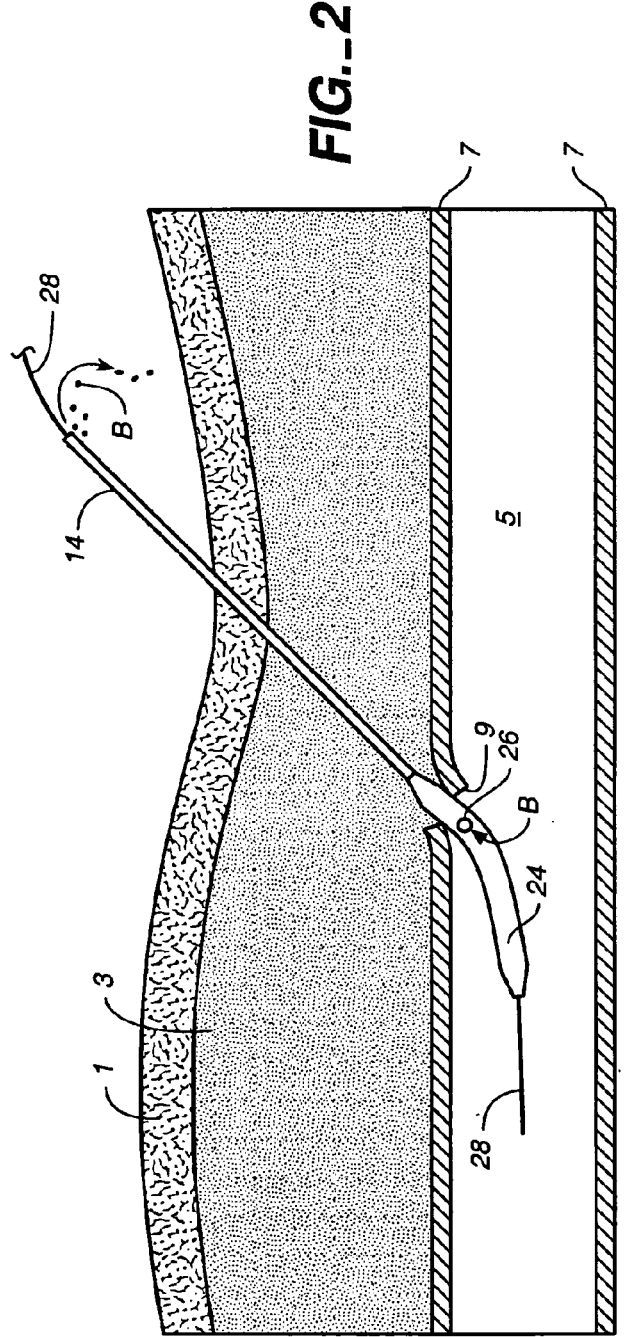
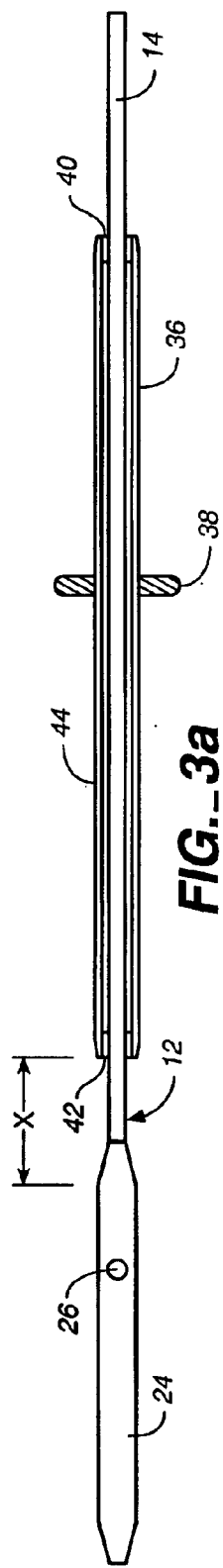

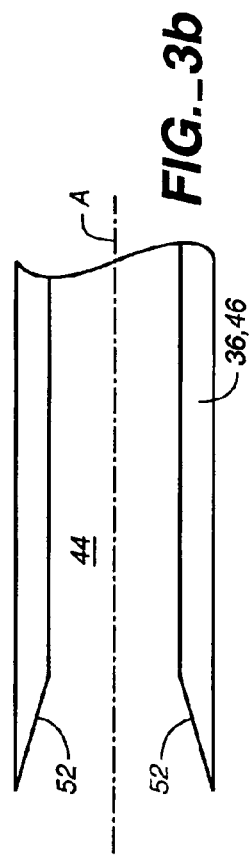
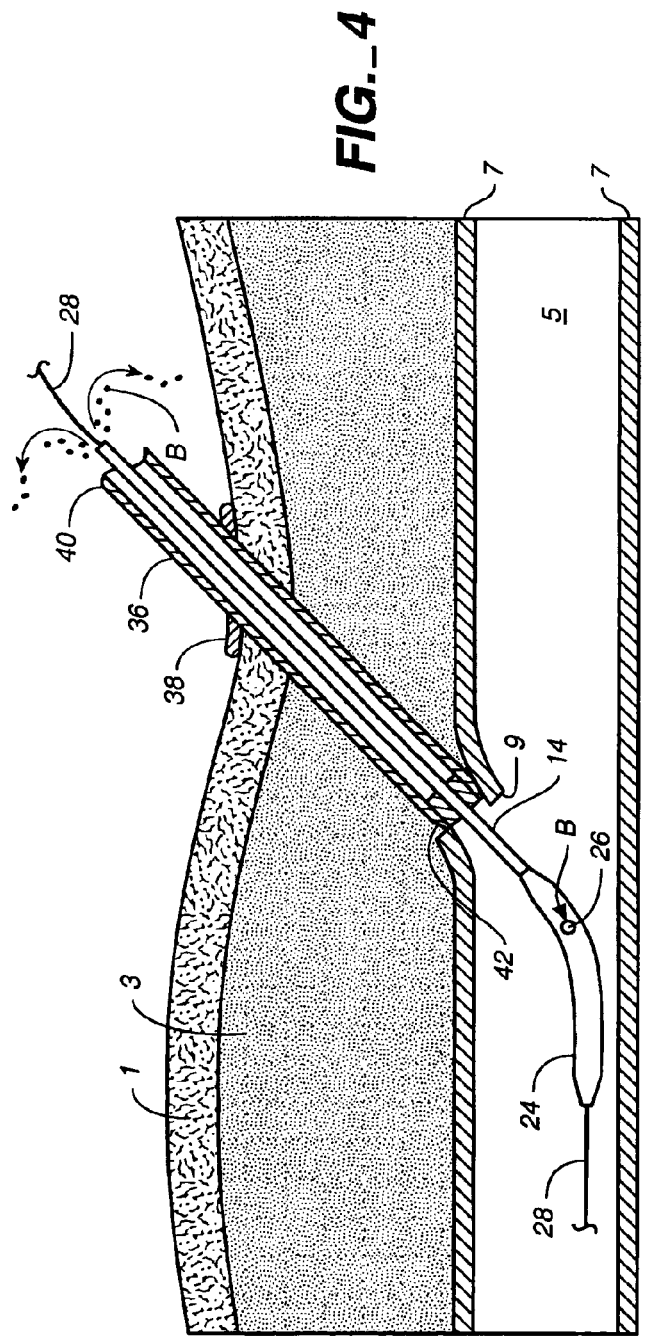

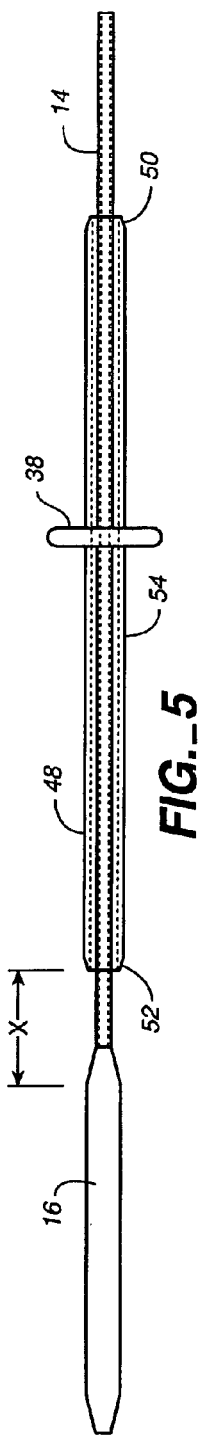
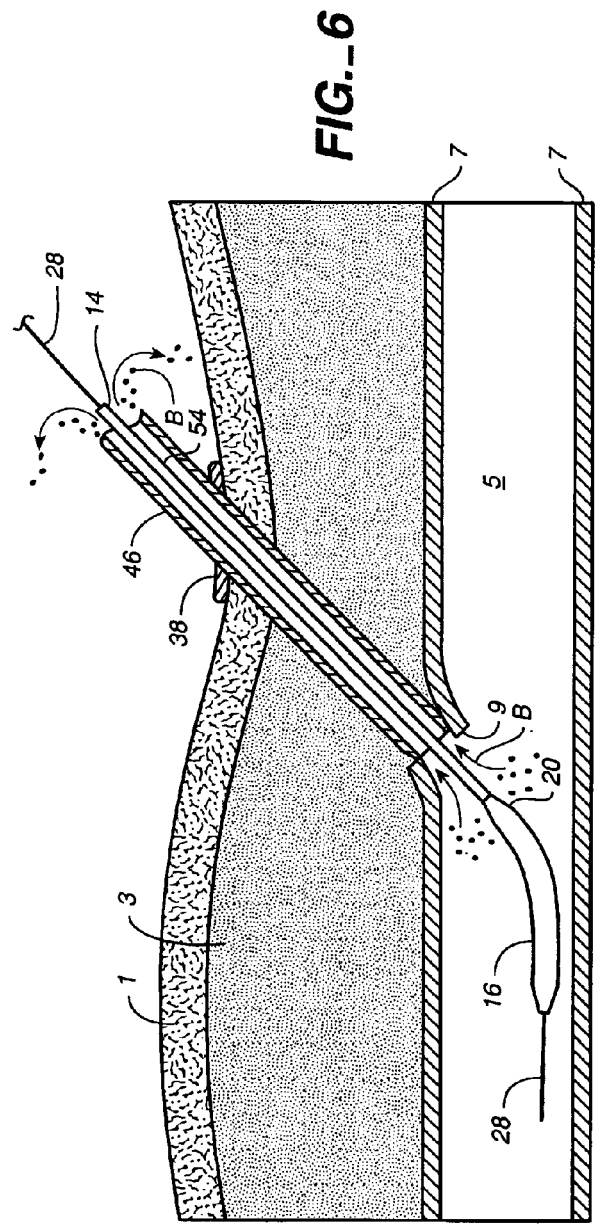

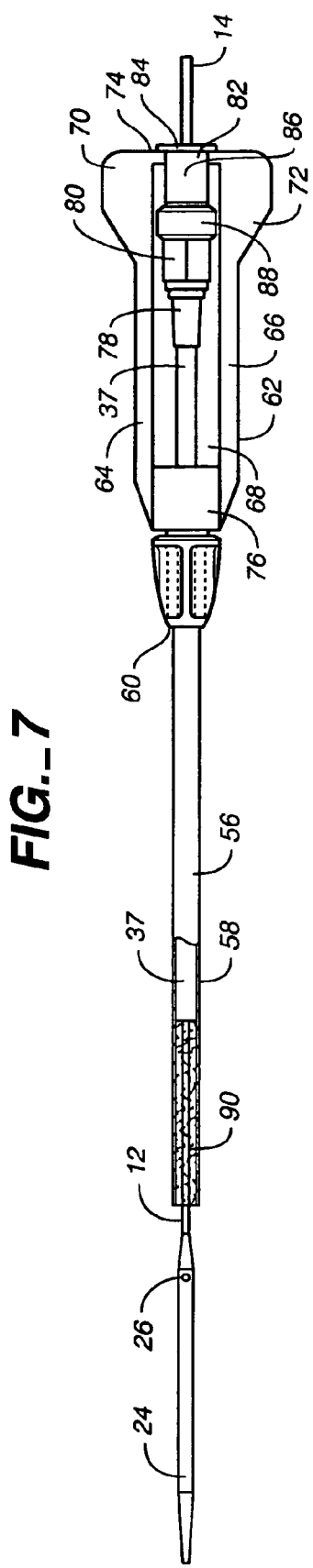
FIG._7

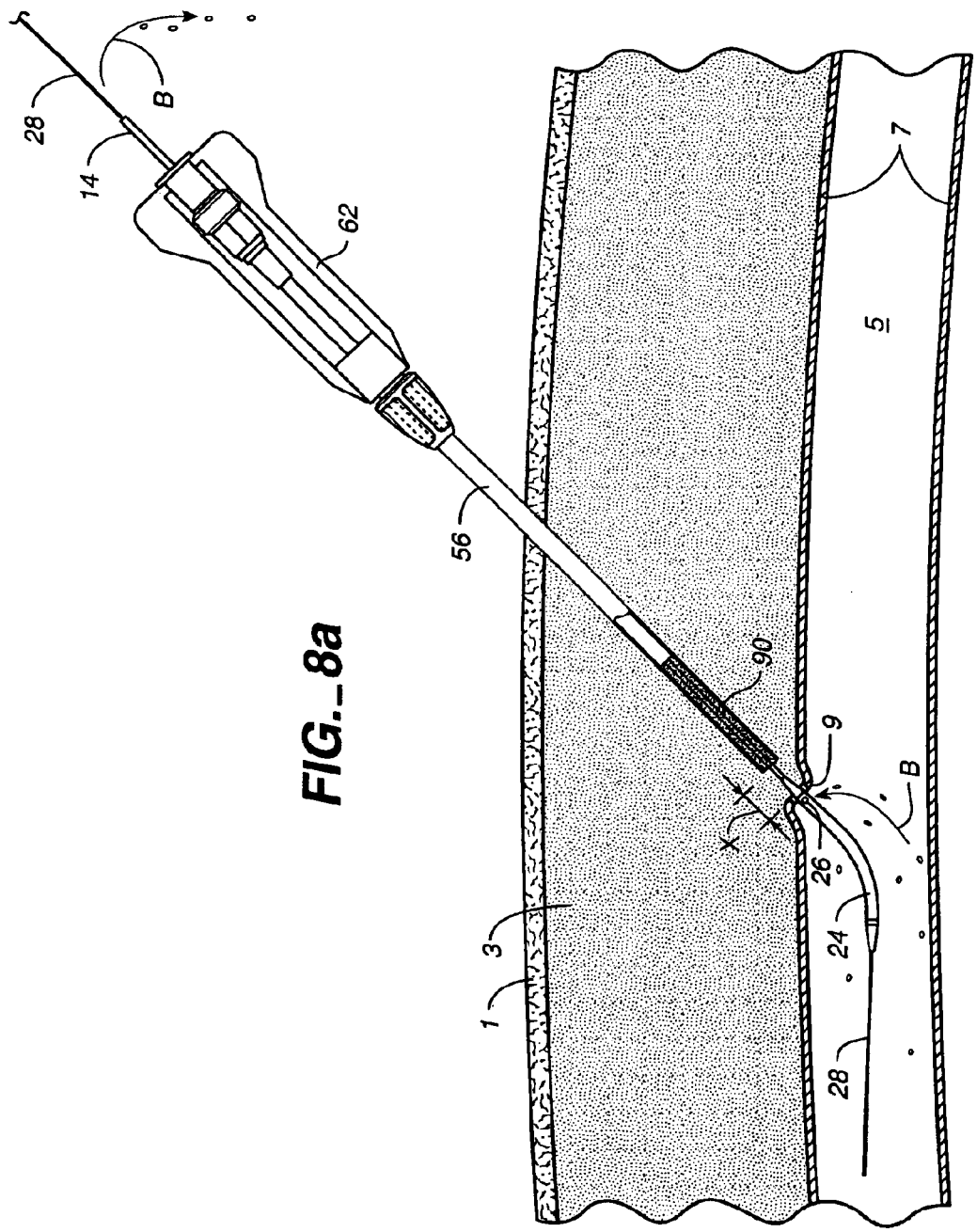
FIG._8a

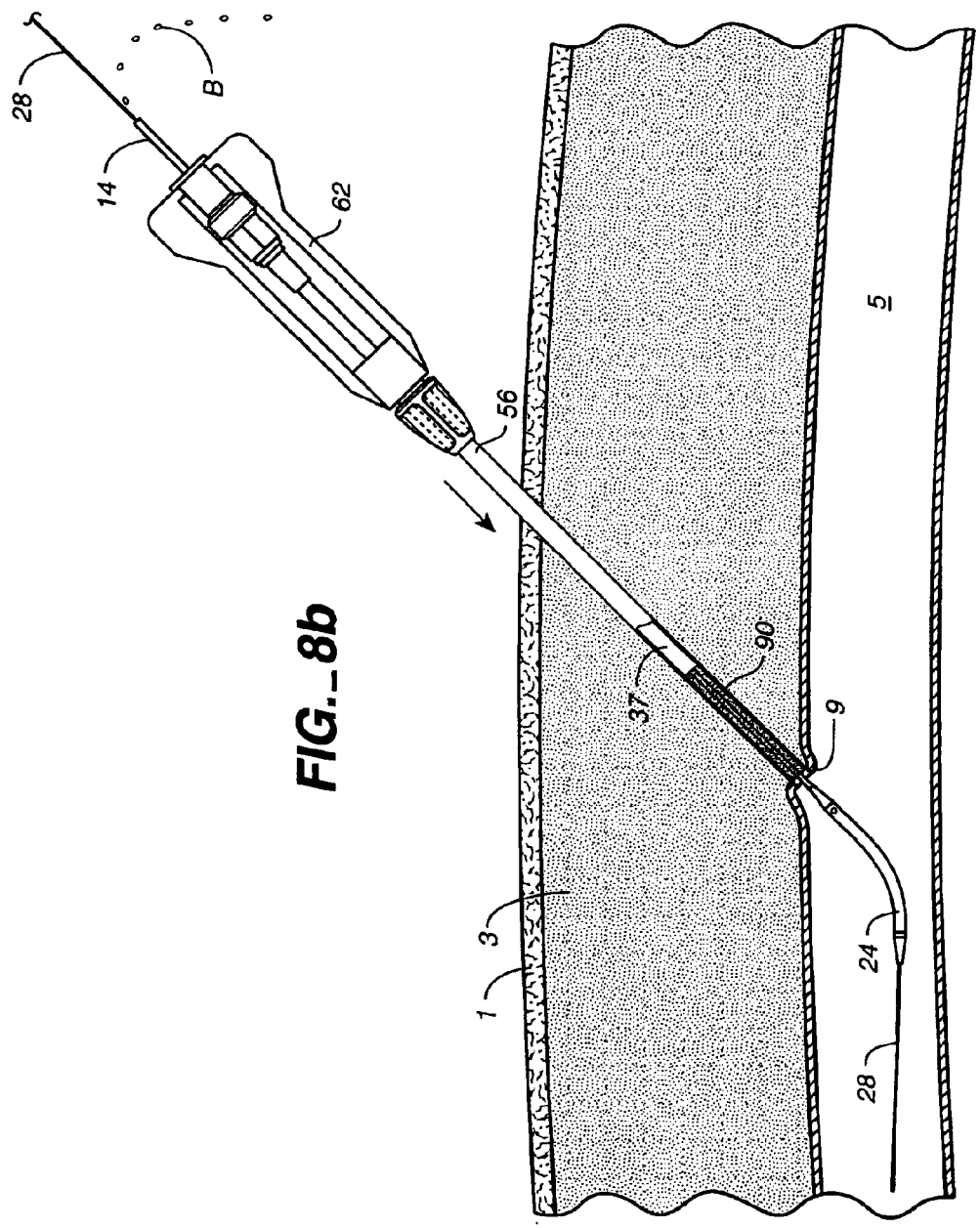
FIG._8b

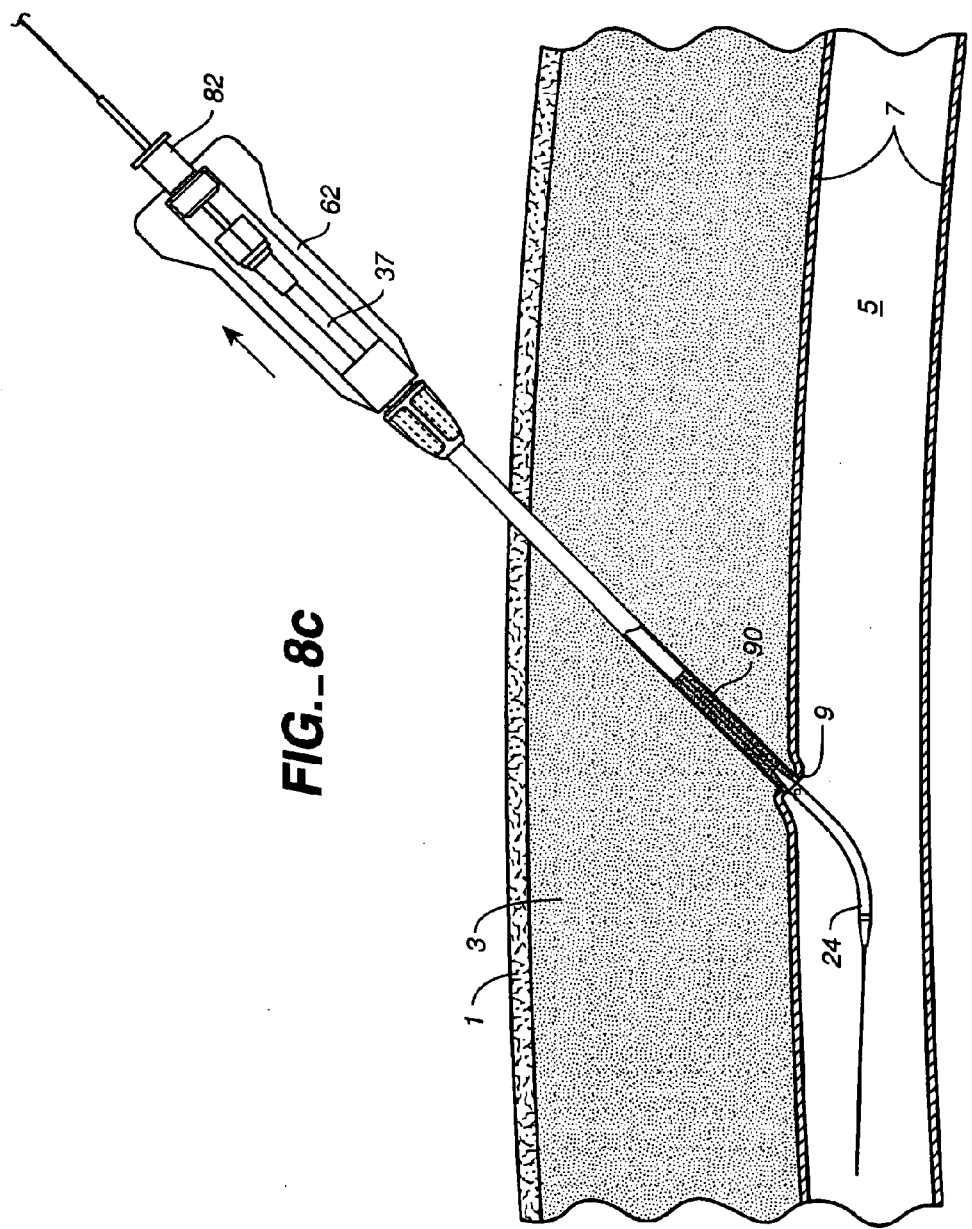

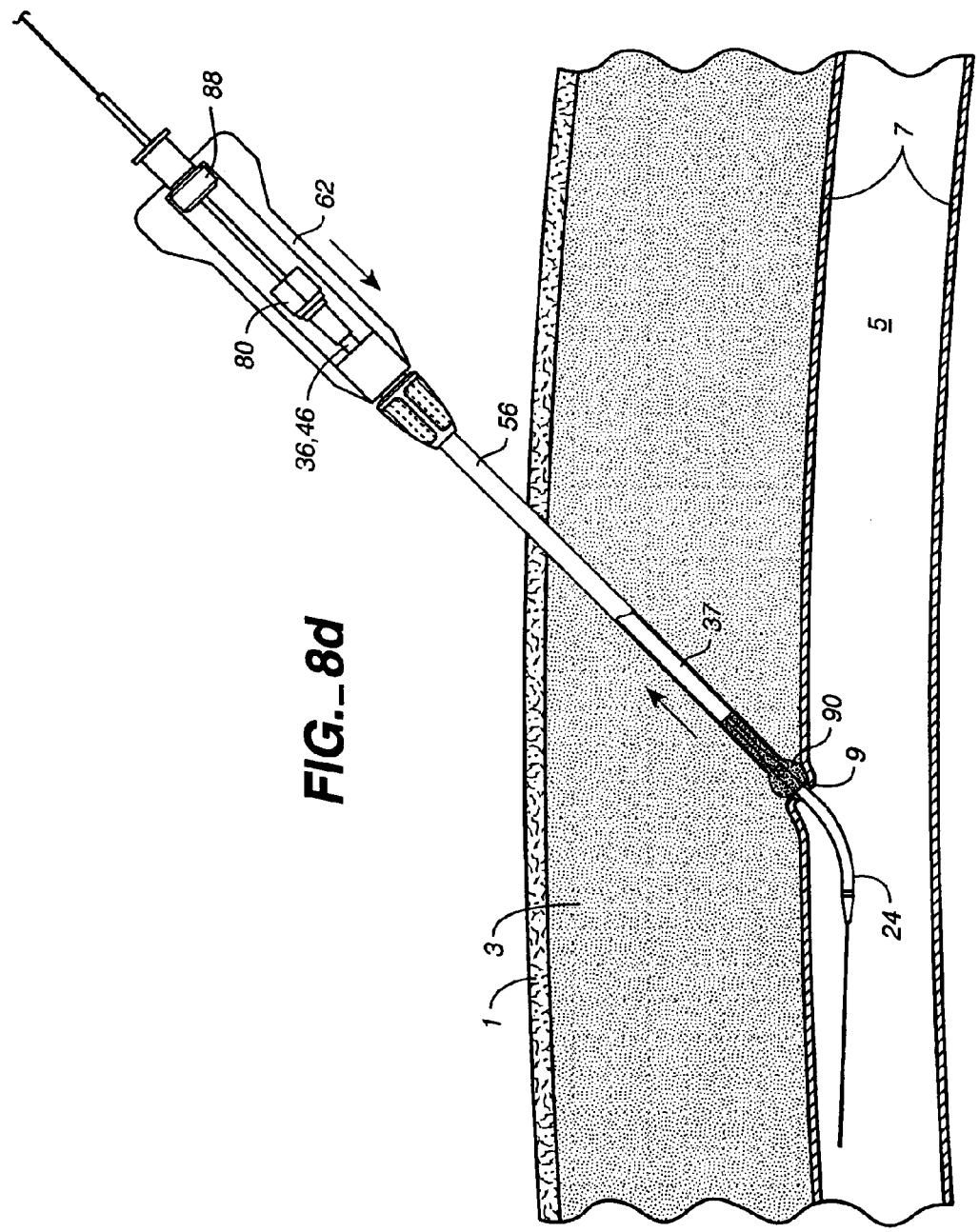
FIG._8d

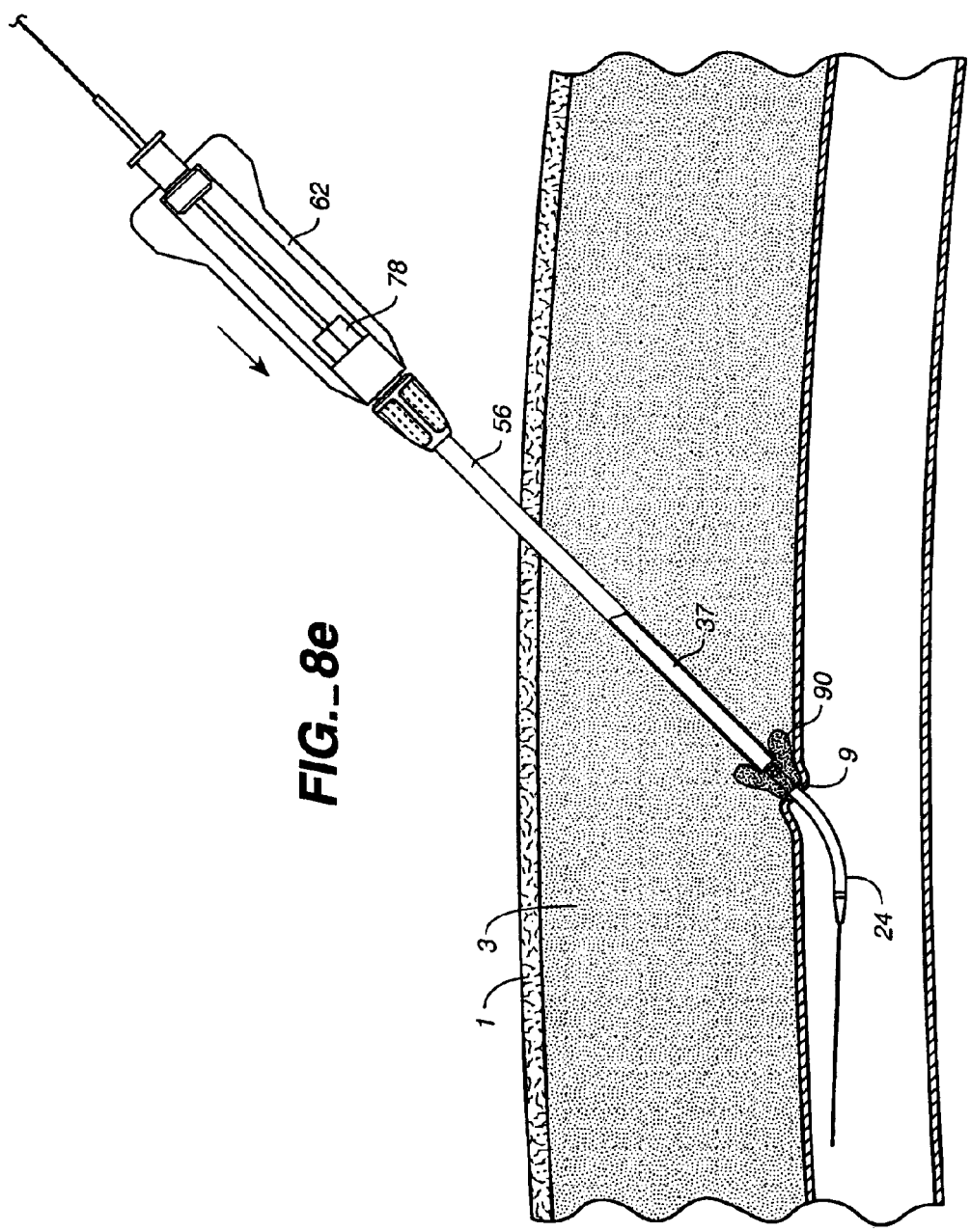
FIG._8e

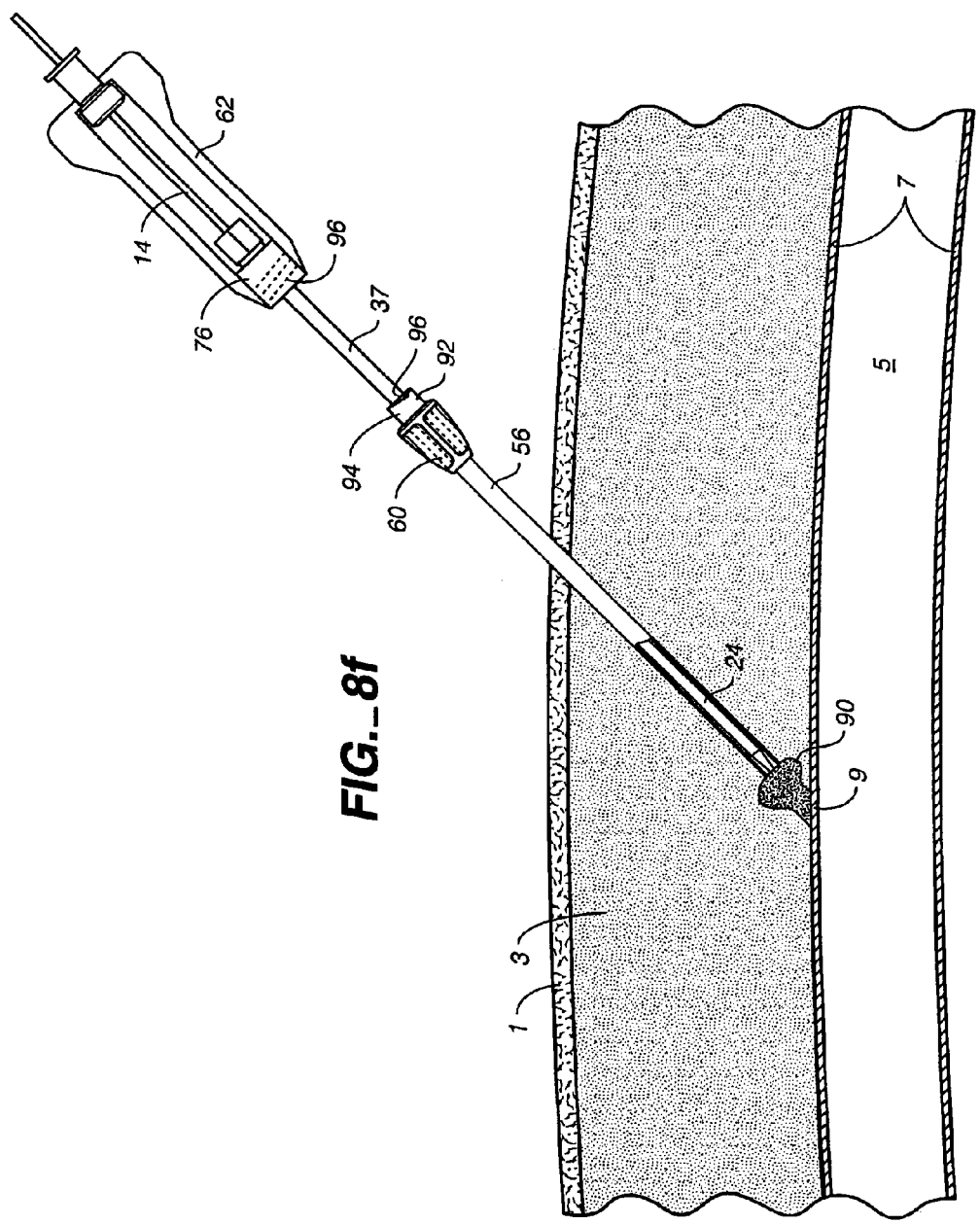
FIG._8f

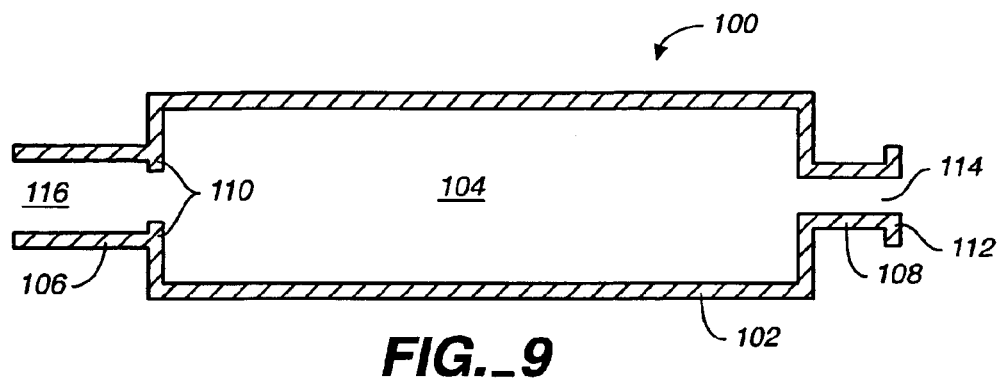
FIG._9
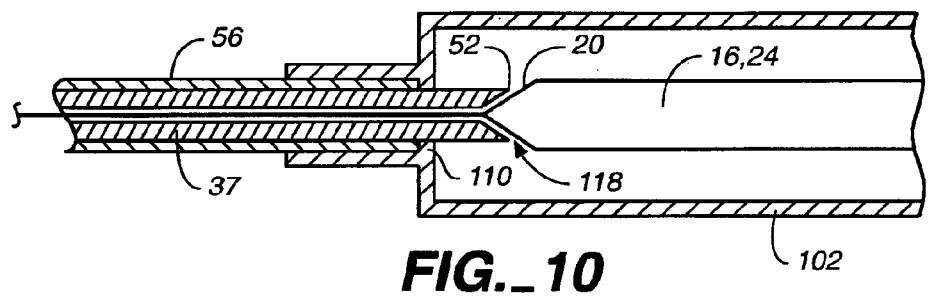
FIG._10
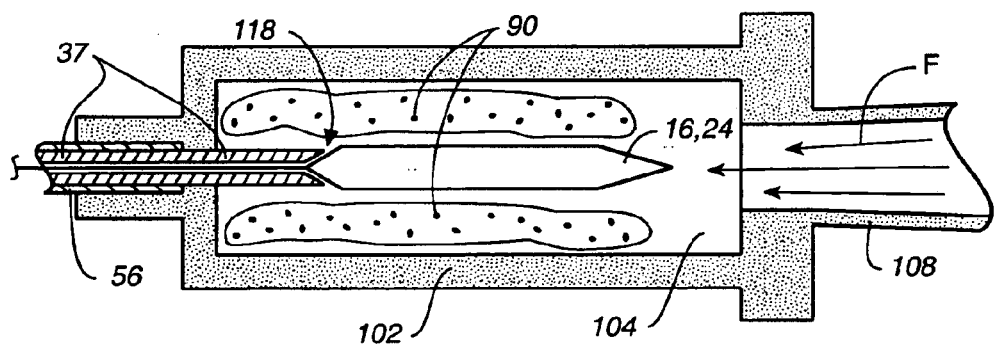
FIG._11

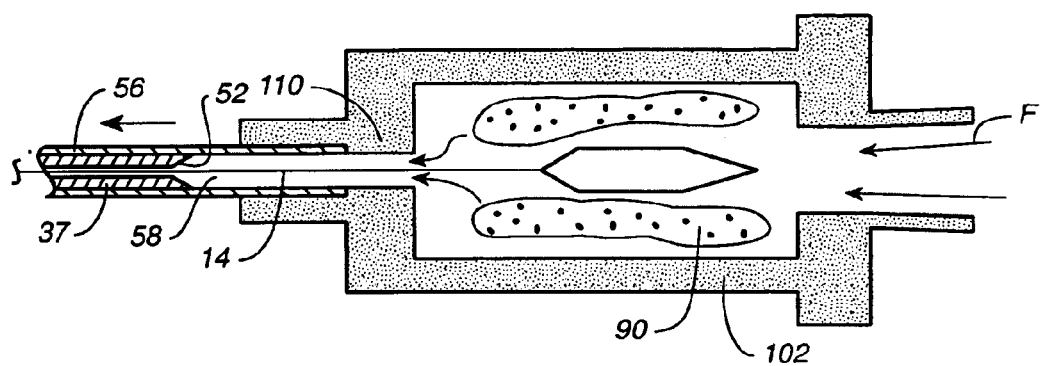
FIG._12
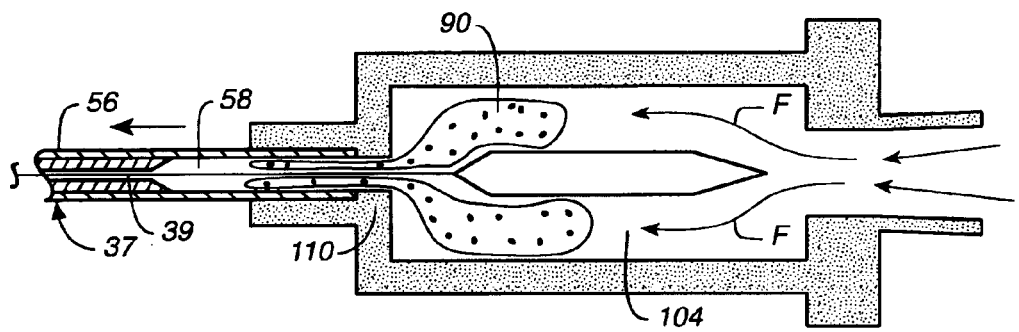
FIG._13
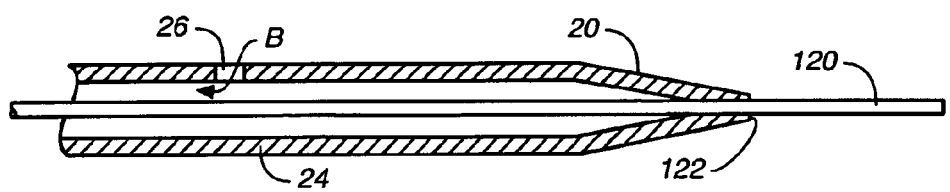
FIG._14

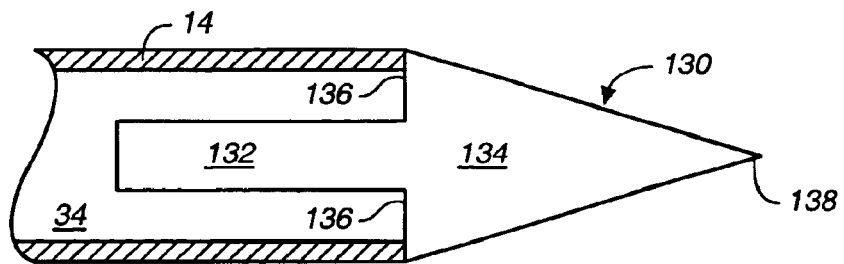
FIG._15
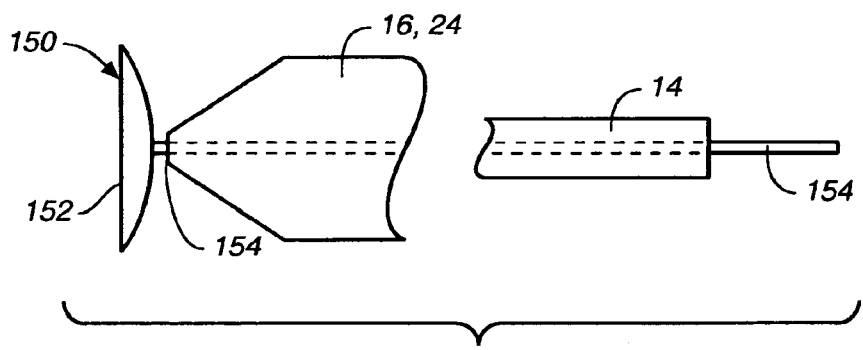
FIG._16
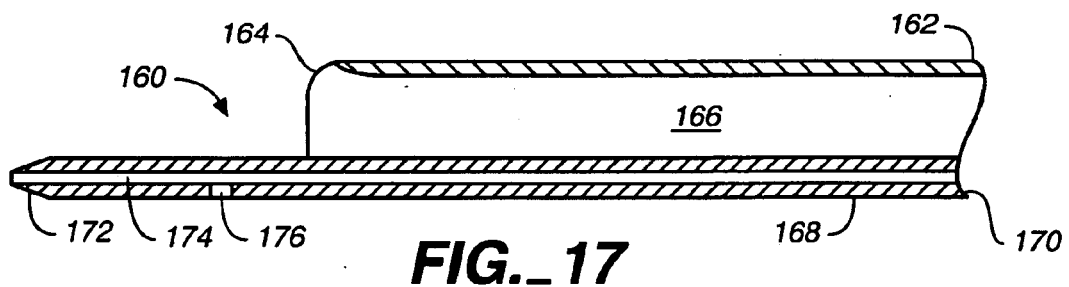
FIG._17

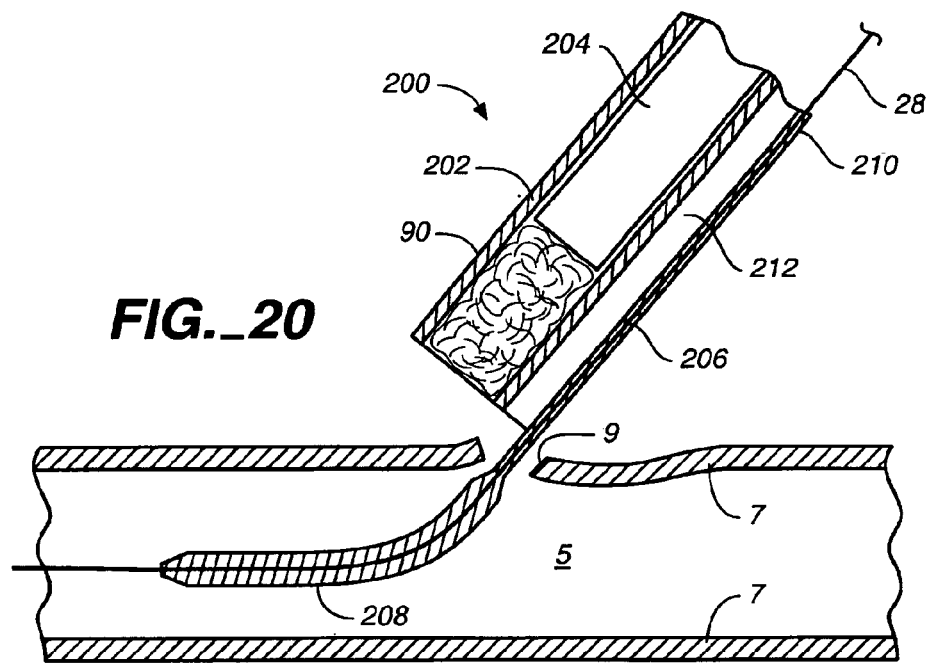
FIG._20
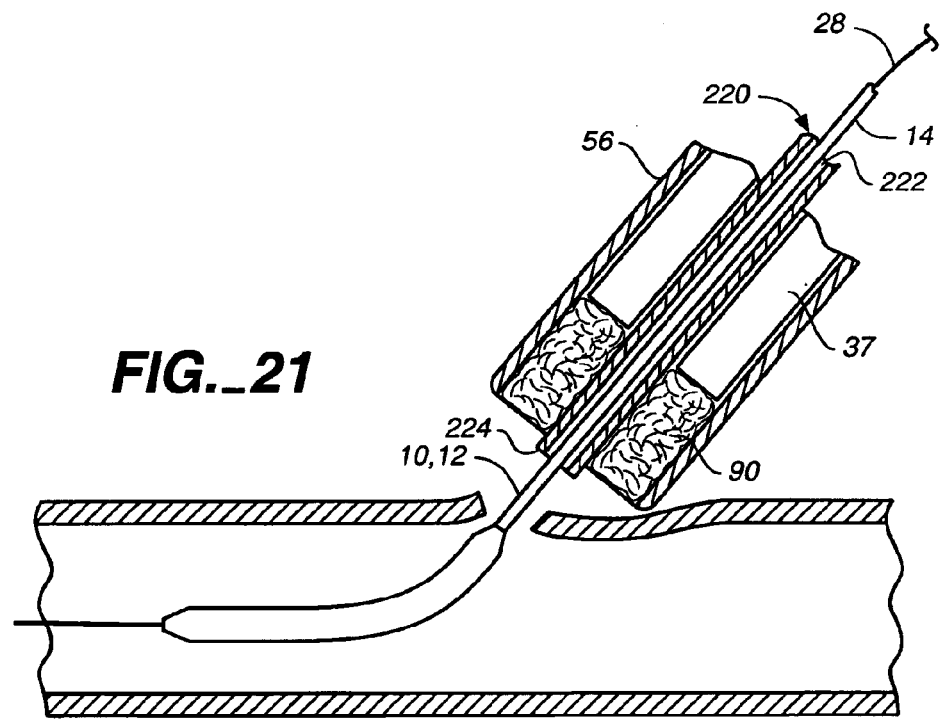
FIG._21

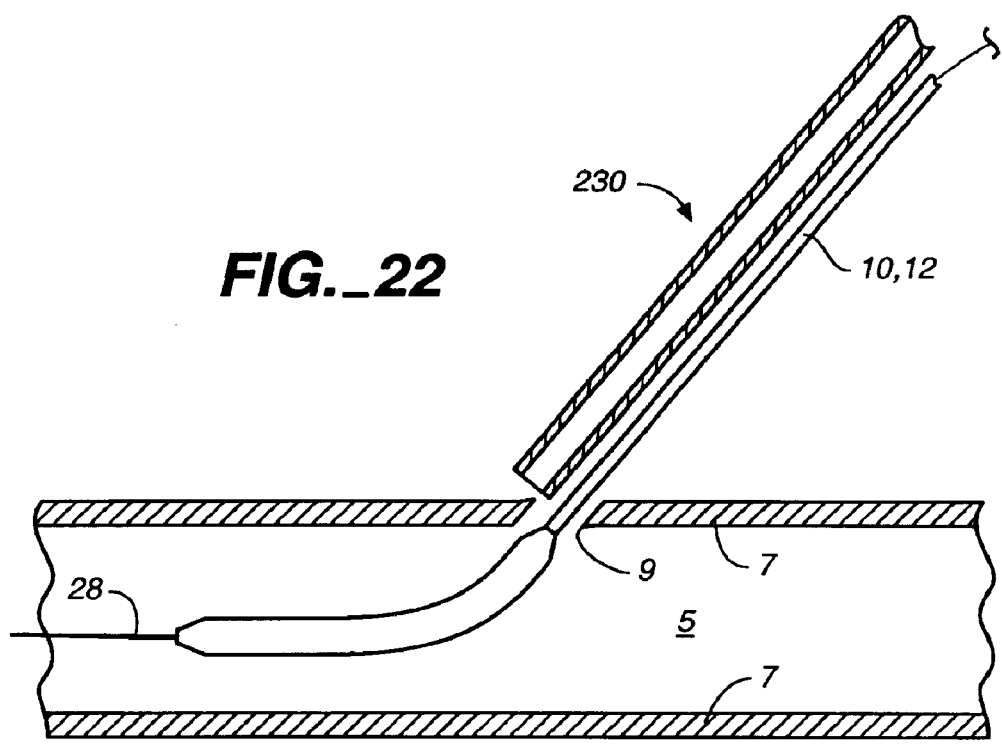
FIG._22

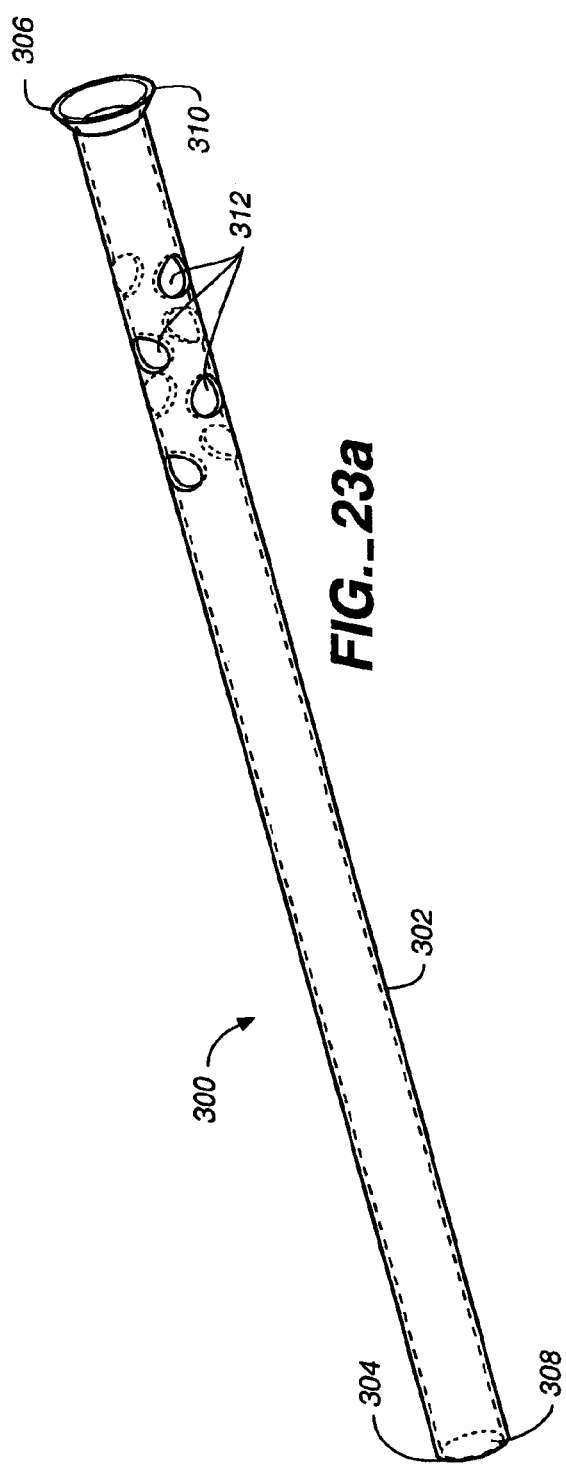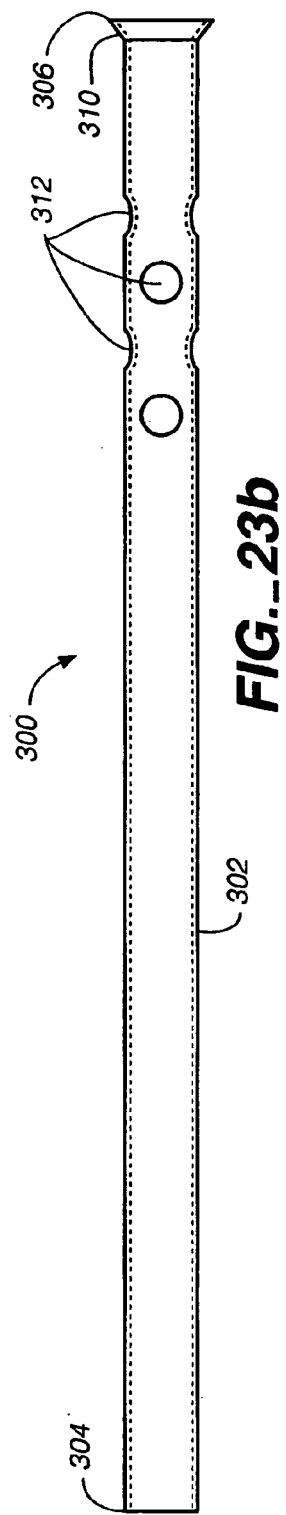

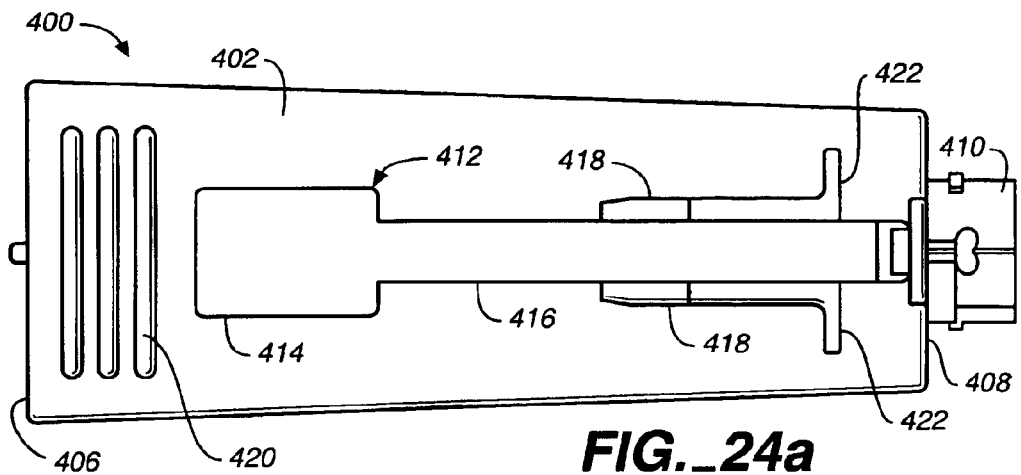
FIG._24a
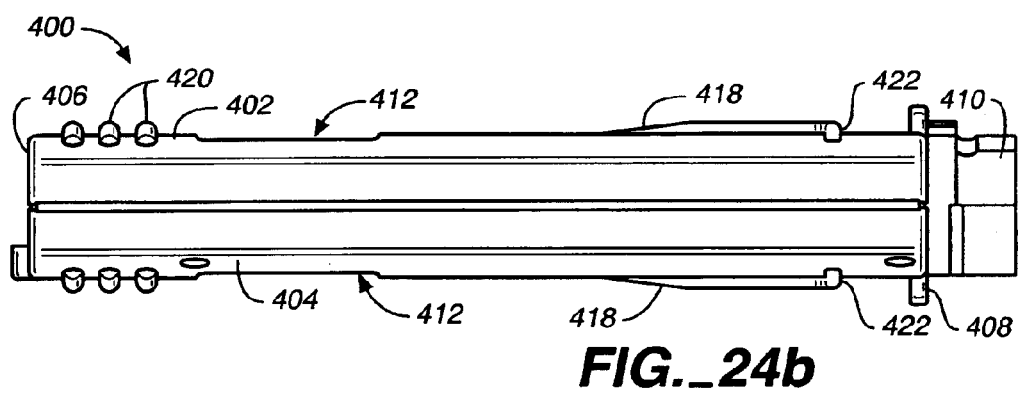
FIG._24b
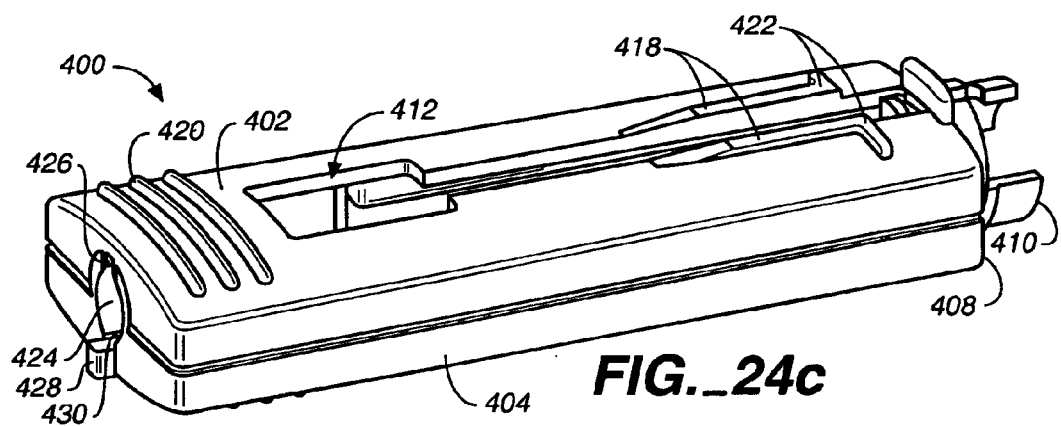
FIG._24c

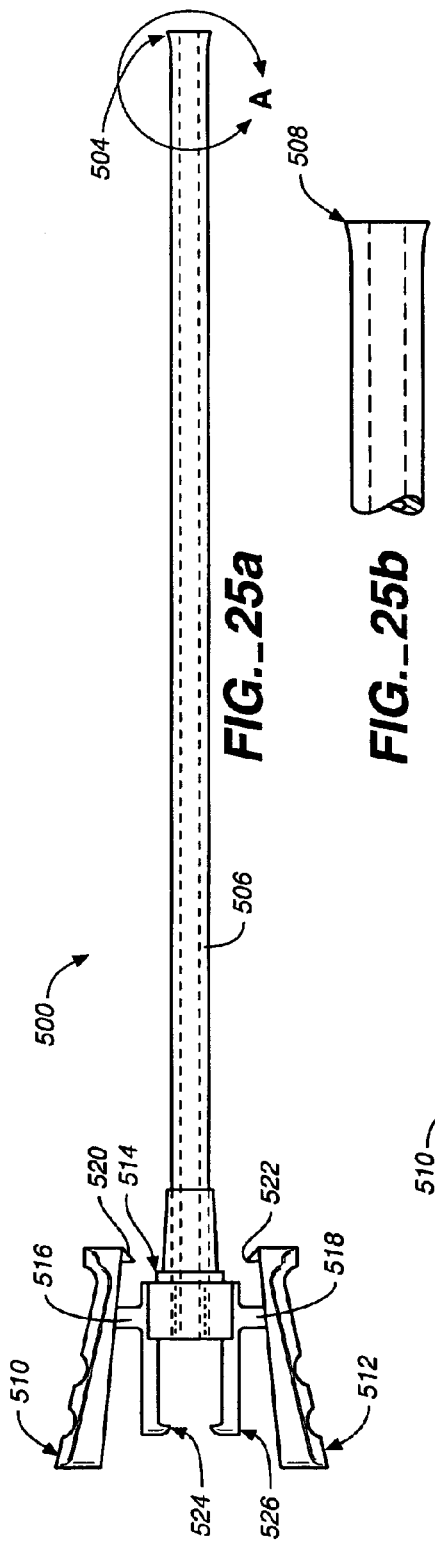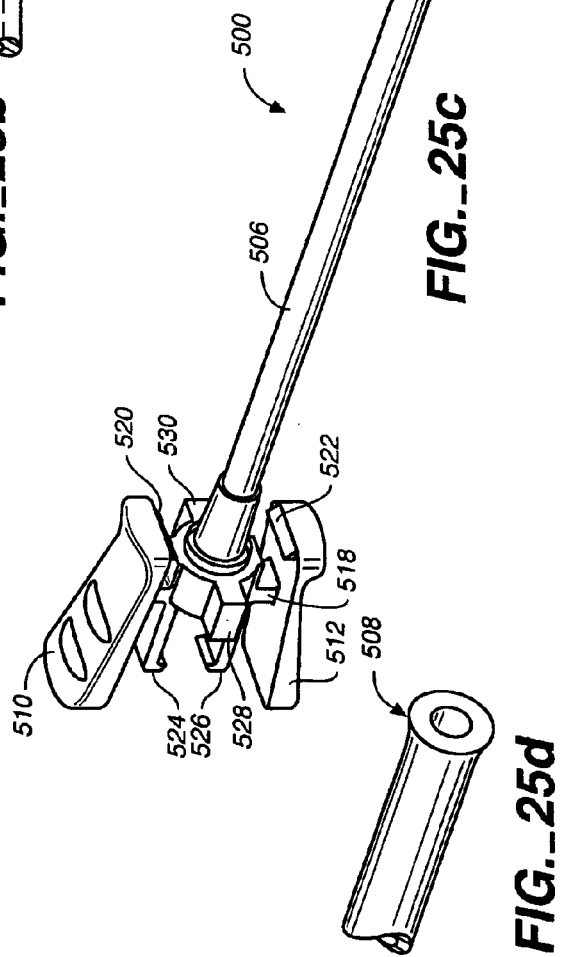
FIG._25a
FIG._25b
FIG._25c
FIG._25d

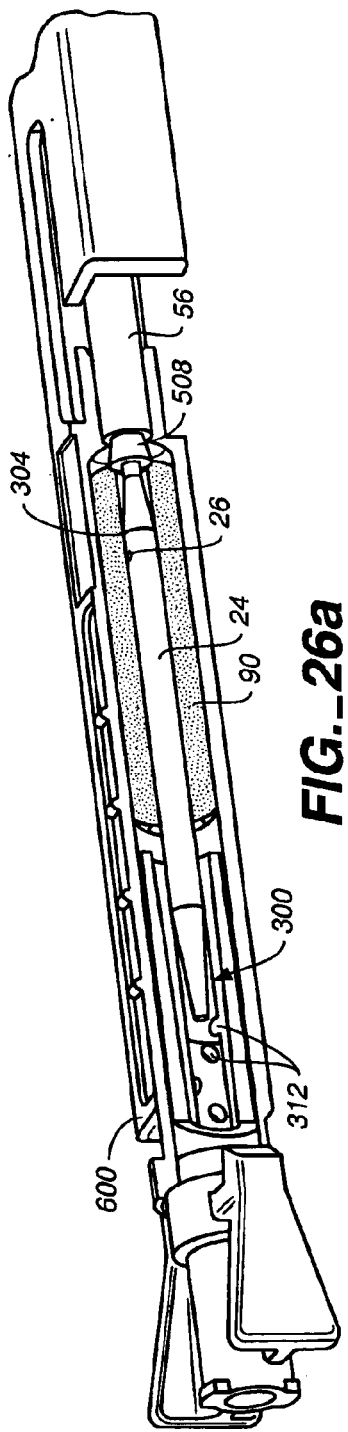
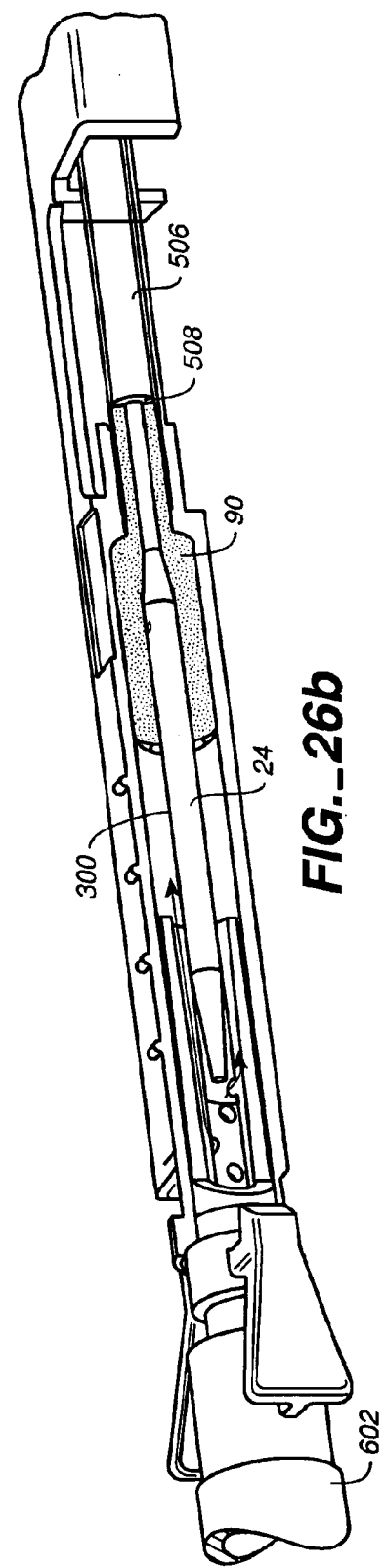

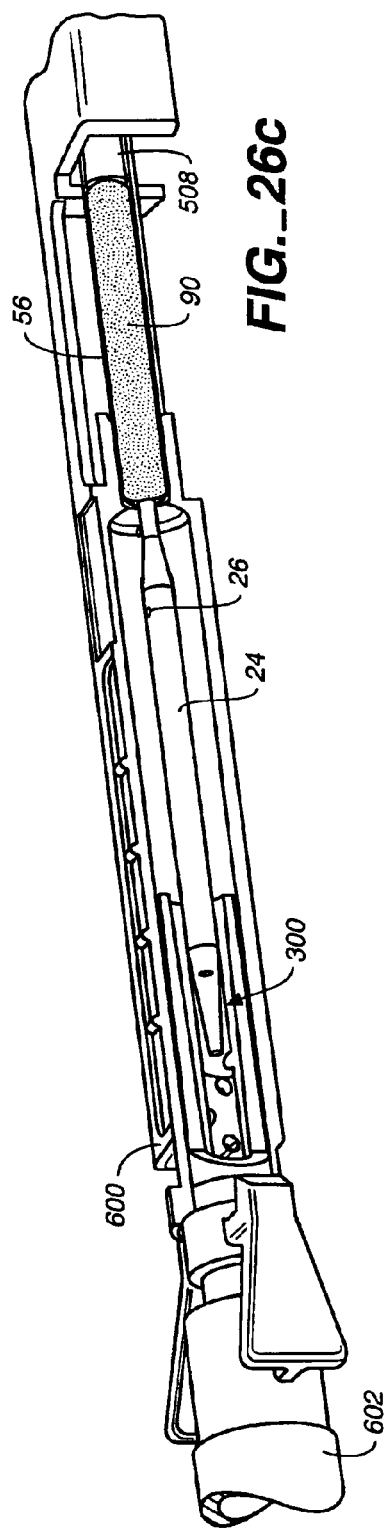
FIG._26c
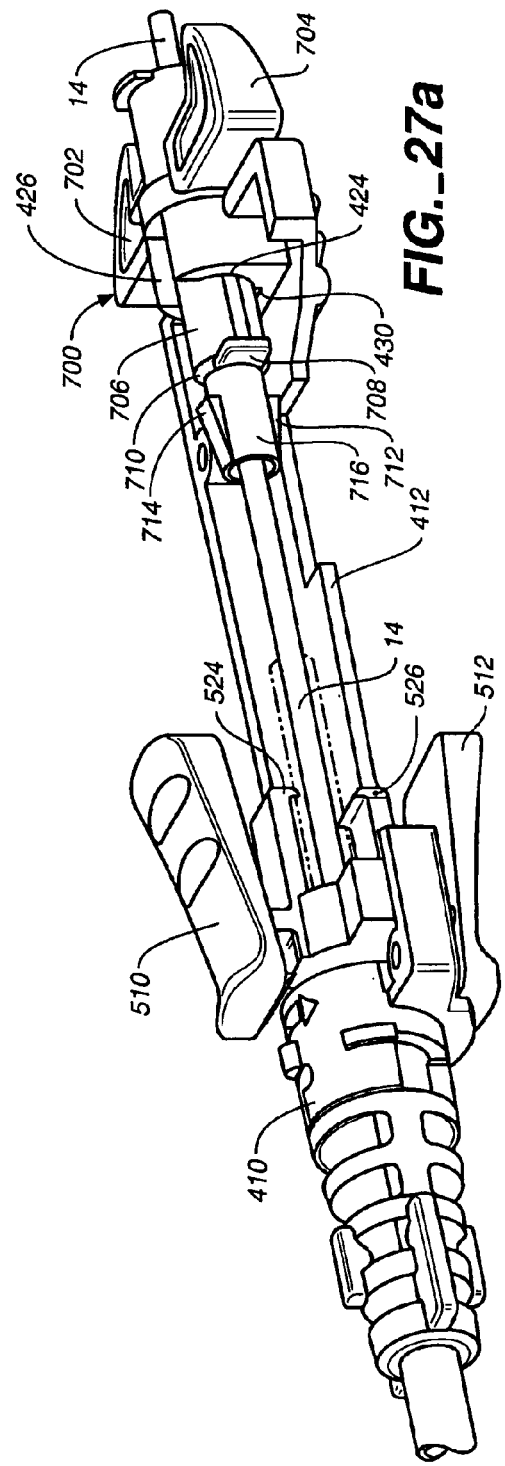
FIG._27a

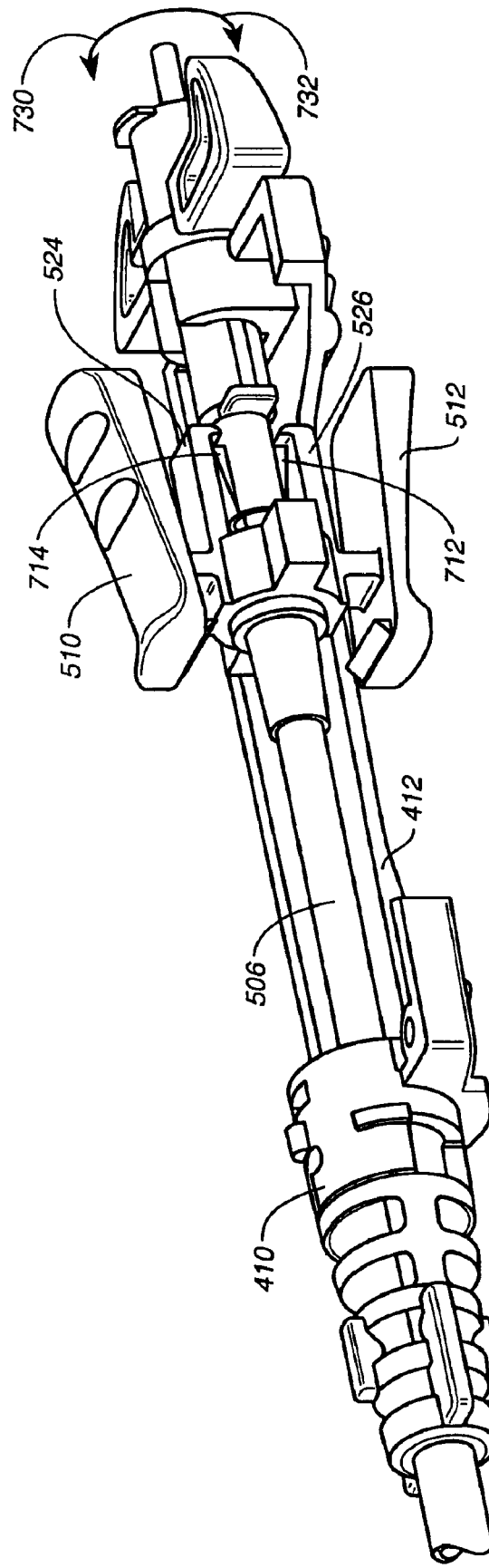
FIG._27b

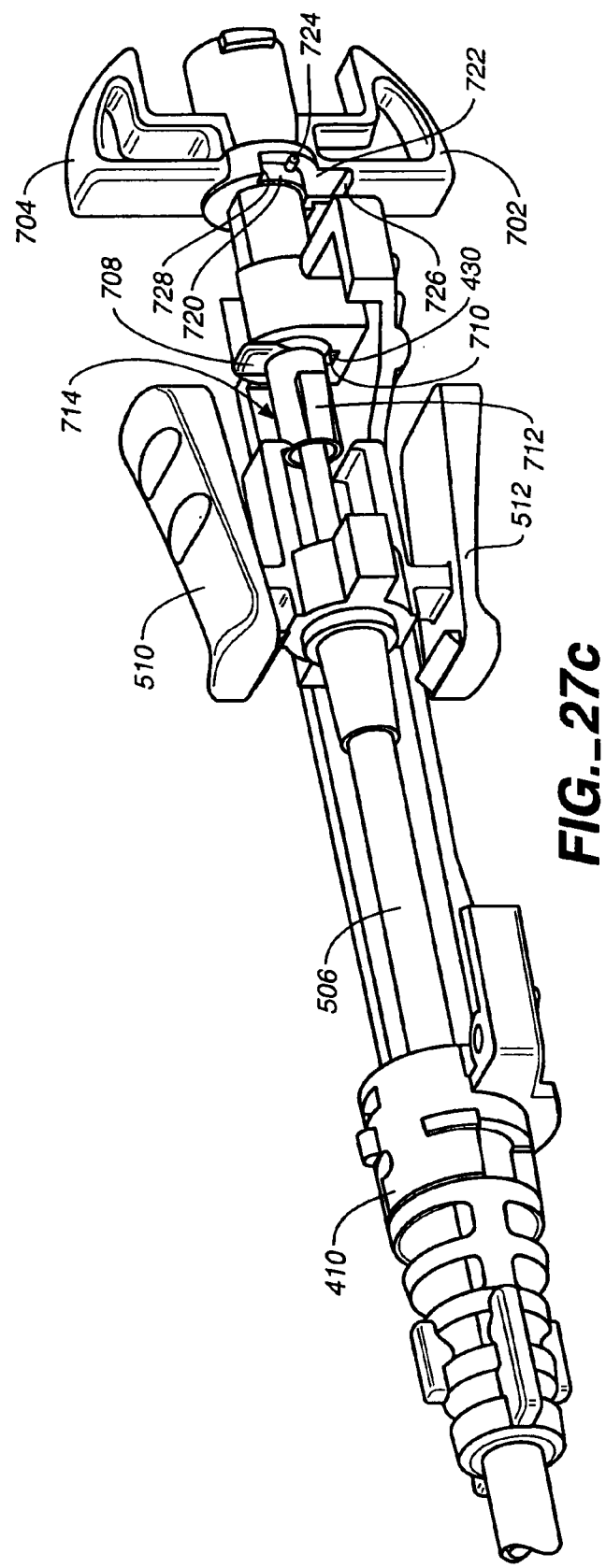
FIG._27c

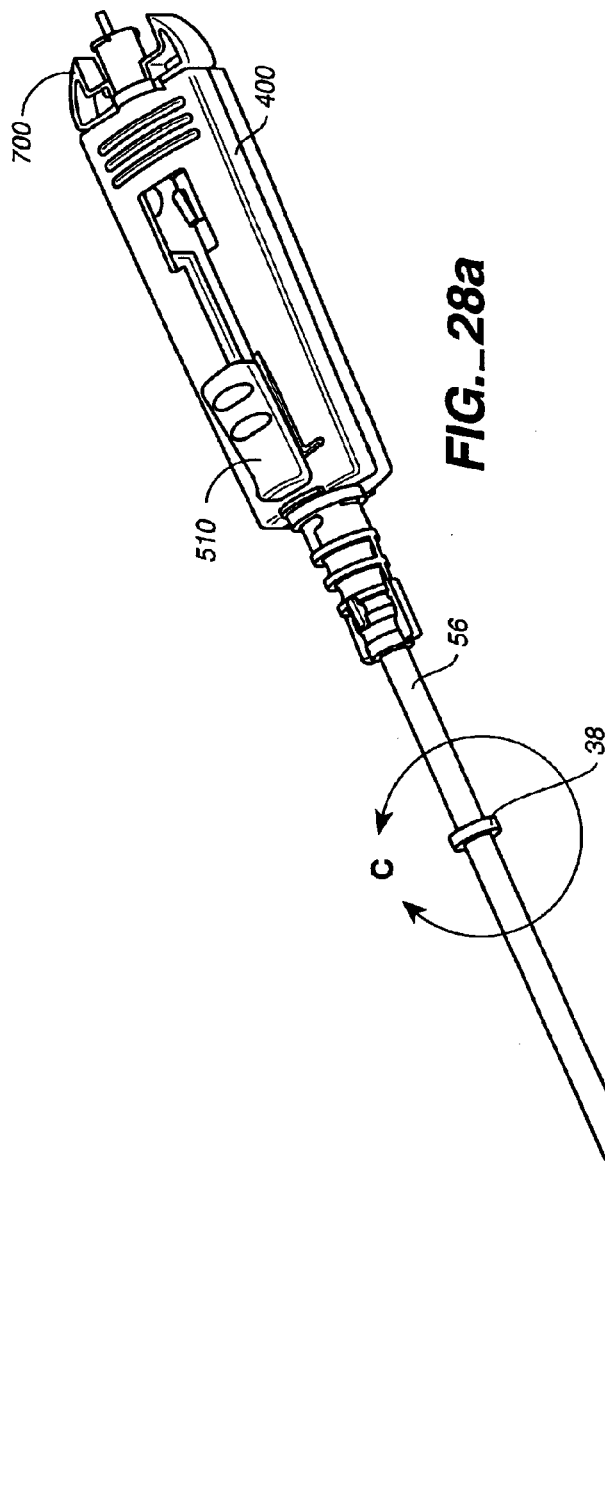
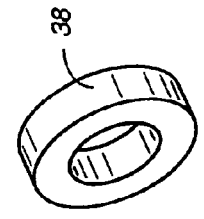
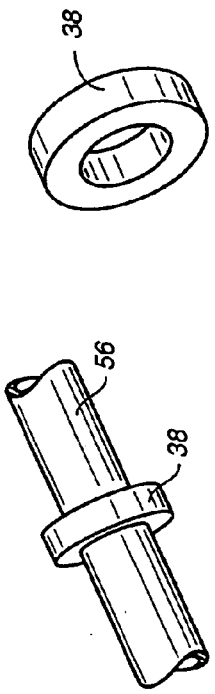
*FIG._28a*
*FIG._28c*
*FIG._28b*

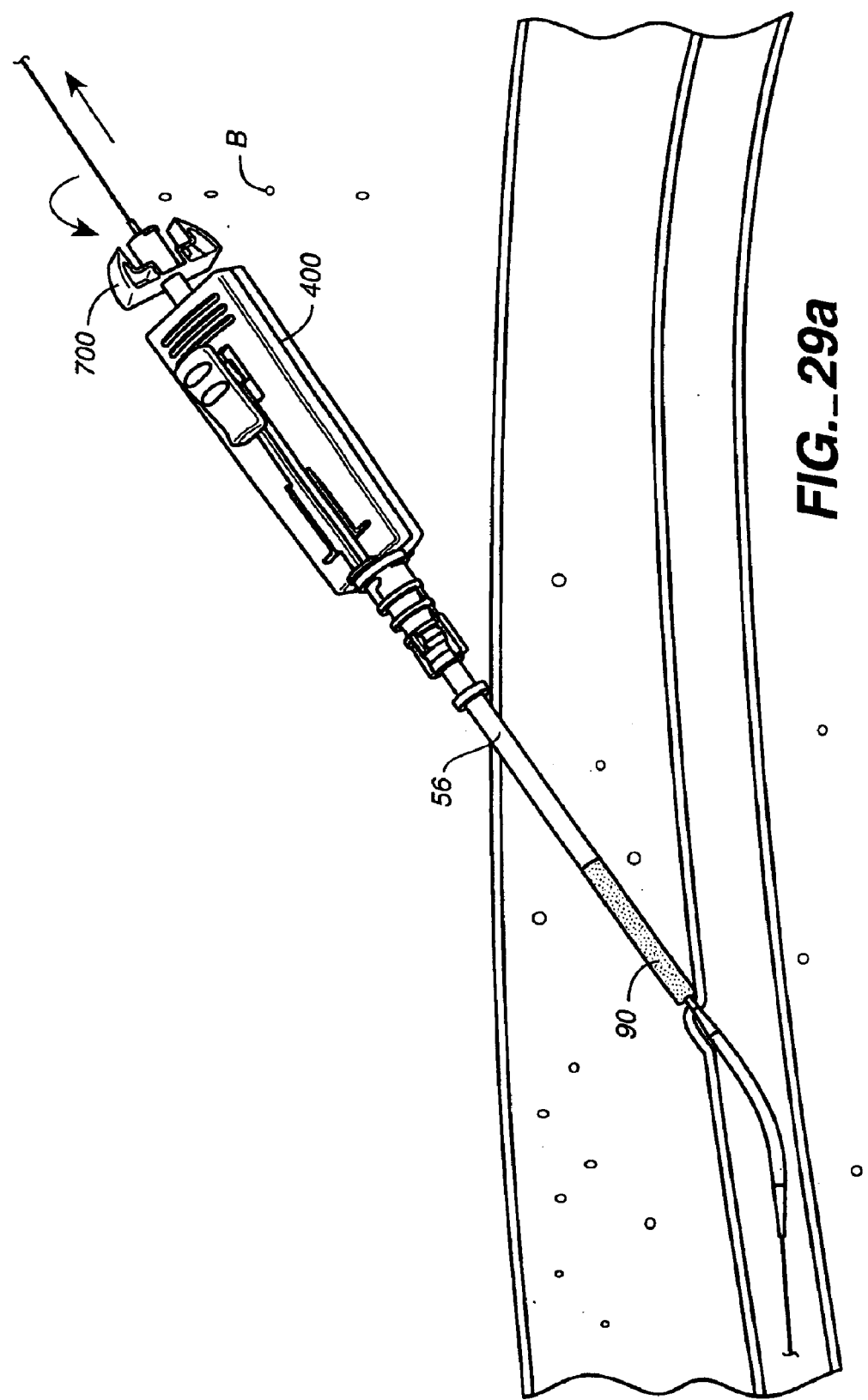

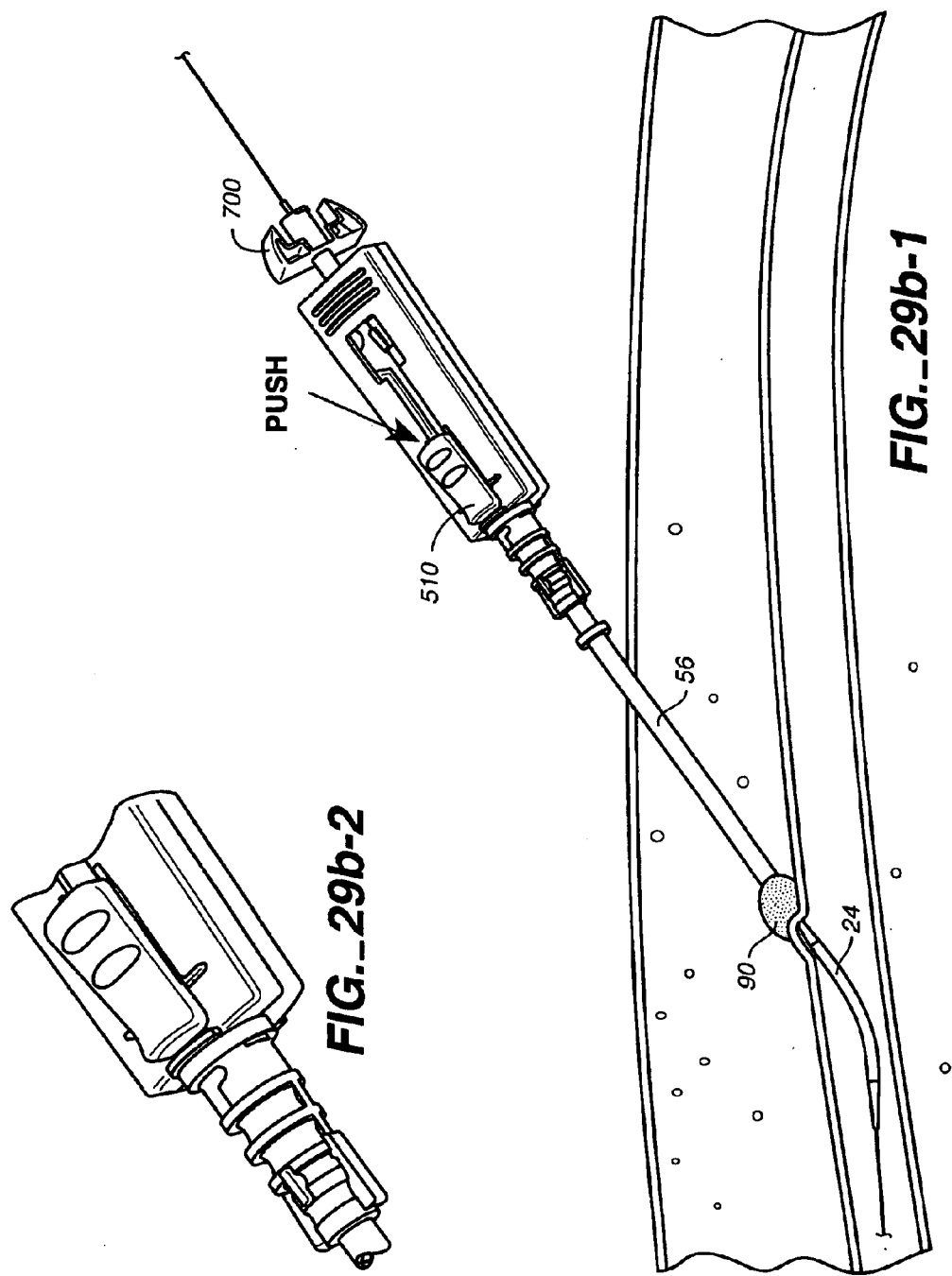

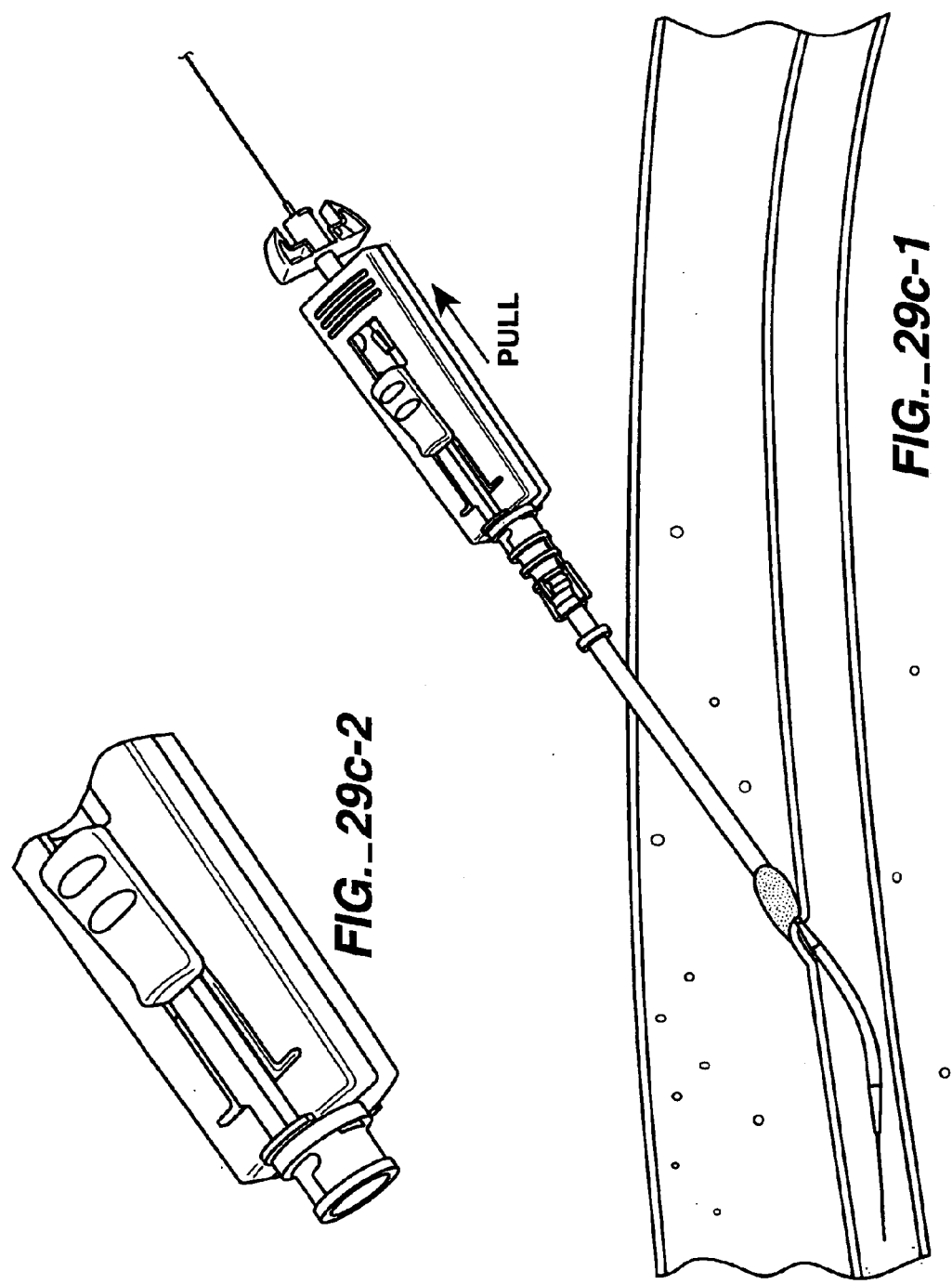

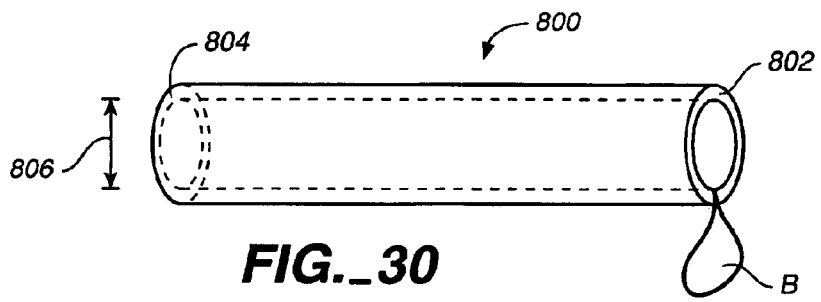
FIG._30
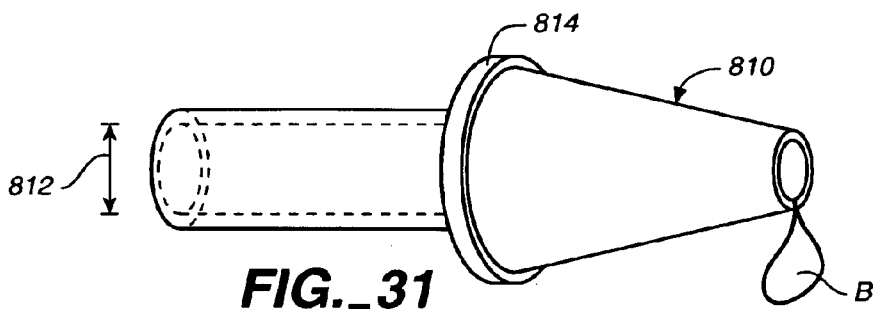
FIG._31
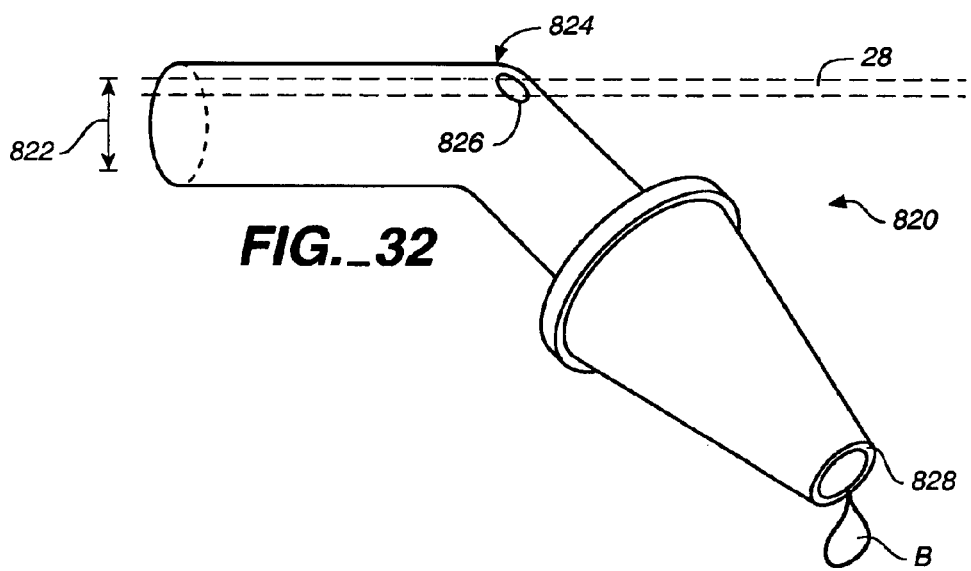
FIG._32

DEPTH AND PUNCTURE CONTROL FOR BLOOD VESSEL HEMOSTASIS SYSTEM

This application is a continuation-in-part of U.S. application Ser. No. 09/621,670 filed Jul. 24, 2000, which is a continuation-in-part of U.S. application Ser. No. 09/613,439 filed Jul. 11, 2000, which is a division of U.S. application Ser. No. 09/071,284 filed May 1, 1998, now U.S. Pat. No. 6,162,192. This application also is a continuation-in-part of U.S. application Ser. No. 09/263,603 filed Mar. 5, 1999, now U.S. Pat. No. 6,315,753, which is a continuation-in-part of the '284 application. The '670 application claims the priority benefit under 35 USC §119(e) to U.S. provisional application Ser. No. 60/156,007 filed Sep. 23, 1999. The disclosures of the foregoing applications are incorporated herein by reference.

BACKGROUND OF THE INVENTION

1. Field of the Invention

The invention relates to closure systems and methods for blood vessel puncture sites.

2. Brief Description of the Related Art

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Such puncture sealing devices are generally used in conjunction with a cannula or arterial dilator which dilates an access tract in the tissue before inserting the sealing device for placing the intraluminal or sealing plug. By using the cannula to dilate the access tract, the sealing device can be easily advanced into the tissue toward the vascular puncture. However, a conventional cannula has either a constant diameter lumen which is sized to closely accommodate a guidewire, or the diameter of the lumen narrows at the distal end. When these conventional cannulas are advanced into the access tract, the cannulas often encounter scar or muscular tissue that requires substantial force to advance the cannula through these layers. In prior conventional cannulae, a cannula which has a constant diameter lumen may enter the vascular puncture while being advanced into the access tract, or the cannula will bounce against a wall of the blood vessel rather than accurately locate the blood vessel wall. Accordingly, the sealing plug may not be accurately placed over the puncture site.

The devices and methods described in the aforementioned '670 application are well-suited for controlling a blood vessel puncture. It has been observed, however, that in some circumstances blood flashing out the proximal end of the device does not form blood drops as readily as would be desired. The bleed-back presented by the devices of the '670 application is detected as it exits the coaxial space created by the inside diameter of the proximal end of the flash tube and the outside diameter of the guidewire. The feedback provided by this configuration can be compromised by several factors, including low surface tension, short length of the proximal flash tube, pooling of blood in the proximal luer, blood running onto the handle, and finally blood oozing from the proximal flash tube that has entered into the tip and/or into the bleed-back hole via tract oozing prior to the bleed-back hole entering the blood vessel lumen. These factors can conspire to make the resulting bleed-back signal challenging to interpret and less meaningful to the casual observer. Additionally, blood running onto the handle is messy and may undesirably wet the user's gloves. Providing a bleed-back system overcoming these limitations would provide significant benefit.

Accordingly, it would be desirable to provide a system for accurately locating the blood vessel wall for properly placing a hemostasis plug over a puncture site.

SUMMARY OF THE INVENTION

According to one aspect of the present invention, an apparatus useful for inhibiting blood loss out a puncture site in a blood vessel wall and for indicating the location of a blood vessel comprises a vent tube including a tubular shaft having a proximal end, a distal end, and a lumen extending longitudinally between the proximal end and the distal end, and a control head on the distal end of the vent tube shaft, the control head including a proximal end portion, a distal end portion having a distal port, and a central portion between the proximal end portion and the distal end portion, the control head including a lumen extending from the distal port to the vent tube shaft lumen.

According to another aspect of the present invention, a pledget delivery and blood vessel puncture site control system comprises a control tip including a vent tube having a tubular shaft with a proximal end, a distal end, and a lumen extending longitudinally between the proximal end and the distal end, and a control head on the distal end of the vent tube shaft, the control head including an externally tapered proximal end portion, a distal end portion having a distal port, and a central portion between the proximal end portion and the distal end portion, the control head including a lumen extending from the distal port to the vent tube shaft lumen, a pledget pusher positioned around the vent tube shaft, the pledget pusher including a tubular shaft having a proximal end, a distal end, and a lumen extending longitudinally between the pledget pusher proximal end and the pledget pusher distal end, the inner diameter of the pledget pusher lumen being larger than the outer diameter of the vent tube, a delivery cannula positioned around the pledget pusher, the delivery cannula a including a tubular shaft having a proximal end, a distal end, and a lumen extending longitudinally between the delivery cannula proximal end and the delivery cannula distal end, the inner diameter of the delivery cannula lumen being larger than the outer diameter of the pledget pusher, the control head extending distally from the delivery cannula distal end, the delivery cannula distal end extending distally of the pledget pusher distal end.

According to another aspect of the present invention, a method of positioning a pledget adjacent to the exterior surface of a blood vessel puncture site in a patient comprises the steps of advancing a control head of a control tip through the puncture site and at least partially into the blood vessel, the control tip including a proximal portion extending out of the puncture site and out of the patient, advancing an assembly over the control tip proximal portion and adjacent to an exterior surface of the blood vessel, the assembly including a delivery cannula having a lumen, a pledget pusher in the delivery cannula, and a pledget in the delivery cannula, proximally retracting the control head to engage the pledget, and expelling the pledget from the delivery cannula.

According to yet another aspect of the present invention, a method of measuring the distance between an epidermal outer surface and the outer surface of a blood vessel, the blood vessel having a puncture therethrough at a puncture site, comprises the steps of advancing a control tip through subcutaneous tissue and into the blood vessel through the puncture, advancing a tubular shaft over the control tip until a distal end of the tubular shaft engages the outer surface of the blood vessel, and positioning a marker along the tubular shaft against the epidermal outer surface.

According to yet another aspect of the present invention, a method of at least partially controlling blood flow through a puncture site in a blood vessel wall comprises the steps of inserting a control tip through the vessel wall at the puncture site and at least partially into the blood vessel, and positioning a pledget adjacent to an outer surface of the blood vessel wall at the puncture site with the control tip still at least part in the vessel puncture site.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 1a illustrates a first exemplary embodiment of a control tip in accordance with the present invention;

FIG. 1b illustrates a second exemplary embodiment of a control tip in accordance with the present invention;

FIG. 1c illustrates an enlarged cross-sectional view of a third exemplary embodiment of a control tip in accordance with the present invention, taken at line 1—1;

FIG. 1d illustrates an enlarged cross-sectional view of a third exemplary embodiment of a control tip in accordance with the present invention, taken at line 1—1;

FIG. 2 schematically illustrates portions of a system in accordance with the present invention positioned in a blood vessel of a patient;

FIG. 3a illustrates a side elevational view of portions of a first exemplary system in accordance with the present invention;

FIG. 3b illustrates an enlarged cross-sectional view of a portion of the exemplary embodiment of a pusher illustrated in FIG. 3a in accordance with the present invention;

FIG. 4 schematically illustrates portions of the first embodiment, illustrated in FIG. 3a, positioned in a blood vessel of a patient;

FIG. 5 illustrates a side elevational view of portions of a second embodiment of a system in accordance with the present invention;

FIG. 6 schematically illustrates portions of the second embodiment, illustrated in FIG. 5, positioned in a blood vessel of a patient;

FIG. 7 illustrates a side elevational view of a system in accordance with the present invention;

FIGS. 8a–8f illustrate steps of an exemplary method in accordance with the present invention;

FIG. 9 illustrates a cross-sectional view of a pledget hydration chamber in accordance with an exemplary embodiment of the present invention;

FIG. 10 illustrates the chamber of FIG. 9 with portions of a device of FIG. 7;

FIGS. 11–13 illustrate exemplary steps of hydrating, preparing, and positioning a pledget into a delivery device in accordance with an exemplary embodiment of the present invention;

FIG. 14 illustrates a cross-sectional view of yet another embodiment of a control tip device in accordance with the present invention;

FIG. 15 illustrates a cross-sectional view of yet another embodiment of portions of a control tip device in accordance with the present invention;

FIG. 16 illustrates a cross-sectional view of yet another embodiment of portions of a control tip device in accordance with the present invention;

FIG. 17 illustrates a cross-sectional view of yet another embodiment in accordance with the present invention;

FIG. 20 diagrammatically illustrates a cross-sectional view of yet another embodiment in accordance with the present invention in one preferred use;

FIG. 21 diagrammatically illustrates a cross-sectional view of yet another embodiment in accordance with the present invention in one preferred use;

FIG. 22 diagrammatically illustrates a cross-sectional view of yet another embodiment in accordance with the present invention in one preferred use;

FIGS. 23a and 23b illustrate views of a tube component useful in yet another embodiment of the present invention;

FIGS. 24a–24c illustrate top plan, side elevational, and top proximal right hand side perspective views, respectively, of yet another embodiment of a handle in accordance with the present invention;

FIGS. 25a–25d illustrate several views of another embodiment of a pledget pusher in accordance with the present invention;

FIGS. 26a–26c illustrate perspective views, with portions broken away, of a hydration and loading device in accordance with the present invention;

FIGS. 27a–27c illustrate perspective views, with portions broken away, of a handle, proximal hub of a control tip, and proximal hub of a pledget pusher in accordance with the present invention;

FIGS. 28a–28c illustrate a collar in accordance with the present invention;

FIGS. 29a–29c illustrate several steps in an exemplary method in accordance with the present invention; and FIGS. 30–32 illustrate three embodiments of a bleed-back control device in accordance with the present invention.

DESCRIPTION OF PREFERRED EMBODIMENTS

Figure 18:
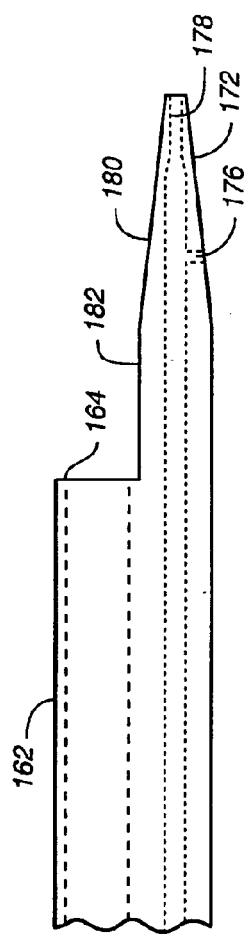
FIG. 18 illustrates a cross-sectional view of yet another embodiment in accordance with the present invention.

Referring to the drawing figures, like reference numerals designate identical or corresponding elements throughout the several figures.

In the context of the present invention, "pledget" means a piece of sponge formed into a generally elongated shape having a size which allows delivery in a hydrated state through a delivery cannula or introducer to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which, when implanted within a human or other mammalian body, is absorbed or resorbed by the body.

"Hydrate" means to partially or fully saturate with a fluid, such as saline, water, contrast agent, thrombin, therapeutic agents, or the like.

FIG. 1a illustrates a puncture control tip 10 in accordance with a first embodiment of the present invention. The puncture control tip 10 includes a tubular, hollow puncture control tip shaft 14 which functions as a flash tube, as described in greater detail below. The shaft 14 includes a lumen 34 (see FIG. 1c, for example) which extends longitudinally between proximal and distal ends. For reasons which will be readily appreciated by one of ordinary skill in the art, lumen 34 can optionally be coated or otherwise provided with an interior surface which inhibits blood coagulation. By way of example and not of limitation, the lumen 34 can be coated with material including heparin (e.g., heparinized), tPa, or other functionally similar materials or compounds which inhibit or prevent blood from clotting or otherwise coagulating in the lumen 34.

The puncture control tip 10 includes, at its distal end, a hollow puncture control head 16 mounted or otherwise secured to distal portions of the shaft 14. As illustrated in FIG. 1a, the head 16 includes a distal tapered portion 18, a proximal tapered portion 20, and a center portion 22 between the distal and proximal portions which preferably has a constant outer diameter. Both of the portions 18 and 20 can alternatively be a step, rounded shoulder, or the like. The interior of head 16 is open to the exterior of the head at the distal portion 18 (see, e.g., FIGS. 1c and 1d).

FIG. 1b illustrates another embodiment of a puncture control tip 12 in accordance with the present invention. The control tip 12 is similar to control tip 10, but includes a puncture control tip head 24 which includes a hole 26 which communicates the exterior of the head with the interior thereof and functions as a flash hole or vent for the control tip. According to yet another embodiment, a hole 26' can be included in addition to, and preferably instead of, hole 26. Hole 26' is formed in the shaft 14 proximal of and proximate to the proximal portion 20, and communicates the interior lumen of the shaft with the exterior of the shaft. Turning to FIG. 1c and 1d, further embodiments of heads 16 and 24 are illustrated as cross-sectional views taken at line 1—1 in FIG. 1b. Shaft 14 includes lumen 34 which fluidly communicates the interior 30 of heads 16, 24 with a proximal end of the shaft. The lumen 34 has an inner diameter selected to be larger than the external diameter of a guidewire, preferably an exchange wire 28, used therewith (see FIG. 2). Furthermore, a plurality of holes 26 (not illustrated) can be formed in the control head, circumferentially spaced and at the same longitudinal location as hole 26.

As illustrated in FIG. 1c, head 16, 24 can be relatively thin walled such that the internal dimensions of the interior cavity 30 is larger in center portion 22 than in the distal 18 and proximal 20 portions of the head. As also described briefly above, the distal portion 18 of head 16, 24 includes a distal port 32 having an internal opening diameter $D_1$ also selected to be larger, and preferably only slightly larger, than the external diameter of a wire 28 used with the control tip 10, 12. While the function of port 32 in conjunction with wire 28 will be described in greater detail below, one aspect of the present invention is that by selecting the external diameter of wire 28 and the inner diameter of port 32 to be only slightly different, blood flow into interior 30 of head 16, 24 is greatly restricted, thus allowing the hole 26 to be the sole entrance into the control tip for blood to flow up shaft 14 to indicate that the control tip head has been located in a blood vessel. As illustrated in FIG. 1d, the head 16, 24 can be formed with a thick wall, such that the interior chamber 30 is the same size as port 32.

Preferably, the control tip is formed of a flexible, biocompatible material such as a thermoplastic. By way of example and not of limitation, the material out of which the control tip is formed has a Shore hardness between about 90A–82D, preferably between about 98A–74D, more preferably about 64D.

Turning now to FIG. 2, some functions of control tips in accordance with the present invention can be better appreciated. As discussed above, at the end of a endoluminal, transvascular procedure the practitioner will oftentimes want to seal the access point to the patient's vasculature. As is commonplace when using a Seldinger technique for vascular access, a guidewire, exchange wire, or guide catheter remains in the patient's blood vessel 5 at the end of the procedure. The indwelling device extends through the epidermis layer 1, through the subcutaneous layers 3, and enters the vessel wall 7 at a puncture site 9.

A control tip 12 (as illustrated in FIG. 2, although control tips 10 can also be used) is advanced either through an indwelling guide catheter, or over an indwelling wire 28, until blood B enters hole 26. The blood B flows into interior 30 of the control head 24, through lumen 34 and around the wire 28, and exits the shaft 14 at its proximal end. This flash of blood at the proximal end of shaft 14 gives the practitioner a visual indication that the control tip is seated in the puncture site 9, while the placement of the hole 26 distal of the proximal portion 20 assists in maintaining the puncture site closed during the procedure. As discussed above, because port 32 has an inner diameter selected to be only slightly larger than the outer diameter of wire 28, little or no blood enters into the interior 30 of the head 24 between the wire and port. Also, the distance between the hole 26 and the proximal end of the vent tube 14, and the internal diameter of the vent tube, are selected together to prevent a capillary effect by the inner wall of the vent tube from stopping blood flow while still permitting good flexibility of the vent tube. Additionally, the vent tube 14 can optionally be formed to have a flexibility which changes along its length, e.g., is more flexible at distal portions than at proximal portions. While a gradual distal increase in flexibility is preferred, the change can be more abrupt, such as by forming the vent tube 14 of two distinct tubes of different flexibilities, although this later embodiment is less preferred.

FIG. 3a illustrates an embodiment of a depth marker 36 mounted over a control tip 12 in accordance with the present invention. Marker 36 is a hollow, tubular member preferably shorter than the control tip 12. Marker 36 optionally further includes a collar 38 slidable along the outer surface of the marker. The collar 38 is preferably elastic such that it will engage the exterior of the marker 36 to hold its position on the marker, yet be movable along the marker upon the application of a small force to slide the collar along the marker. Thus, collar 38 can be used as a depth indicator, as described in greater detail below.

The marker 36 includes a proximal end 40, a distal end 42, and an interior lumen 44 extending longitudinally between the proximal and distal ends. The proximal and distal ends of the marker 36 preferably include a seal with the shaft 14 of the control tip 12. The seal between the shaft 14 and the marker 36 can be formed in any suitable way that provides a fluid seal between the marker and the shaft. By way of example and not of limitation, the proximal and distal seals can be formed by forming the marker with a reduced inner diameter at (at least) the proximal and distal ends of the marker, or by including dynamic sealing members, such as O-rings or septa. Preferably, at least the distalmost portions of distal end 42 is slightly rounded to prevent trauma to the vascular tissues with which it comes into contact.

Marker 36 is preferably attached to control tip 12, or less preferably, positioned on the control tip 12 so that it is difficult to slide them longitudinally relative to each other. The distal end 42 is spaced from the elongated central portion 22 of the control head by a distance X, described in greater detail below. Optionally, the control tip and the marker can be interconnected using a releasable proximal connection, e.g. a Touhy-Borst connector (for which the marker would include cross-drilled holes or the like for blood flash), ultrasonic welding, gluing, etc.

FIG. 3b illustrates an enlarged cross-sectional view of a distal end of a marker 36 or 46 in accordance with the present invention. The marker includes an interior lumen 44 which terminates at the distal end 52 of the marker with a countersunk tapered distal port. For reasons which will be explained in greater detail below with reference to FIGS. 5 and 6, the taper of the distal port relative to longitudinal axis A is selected to be very similar to that of the proximal tapered portion 20 of head 16, 24. This aspect of the present invention permits the wall of the marker 36, 46 which forms the port, together with the proximal tapered portion 20, to function as a valve in a manner similar to a needle valve.

FIG. 4 illustrates a control tip 12 used together with a depth marker 36 to control a puncture site 9. When the control tip 12 has been located in the puncture site 9, as shown by the blood flash B out the proximal end of flash tube 14, with the marker 36 on the shaft 14 the practitioner feels the additional resistance offered by the vessel wall 7 to further advancement of the marker upon distal advancement of the control tip/marker assembly. As the distal end 42 of the marker 36 forms a seal with the shaft 14, the distal end 42 can then be used to control the flow of blood out of the puncture site 9, and the control head 24 is pushed slightly distally into the blood vessel 5. Collar 38 can be positioned against the epidermis 1 when the distal end 42 is at the puncture site 9, which permits the collar 38 to mark the distance between the distal end of the marker 36 and the outer surface of the epidermis, thus functioning as a depth indicator of the puncture site.

Turning now to FIGS. 5 and 6, yet another embodiment in accordance with the present invention is illustrated. FIG. 5 illustrates a control tip 10 with head 16 and a marker 46 mounted thereover. Marker 46 is similar to marker 36, described above, but does not include seals at its proximal 50 and distal 52 ends. A lumen 48 extends longitudinally through the marker 46 between the proximal and distal ends and forms an annular space or lumen 54 between the flash tube or shaft 14 and the marker 46. According to a preferred embodiment of the present invention, distal end 52 is tapered as illustrated in FIG. 3b. Marker 46 is affixed to control tip 10 in a fashion similar to marker 36 and control tip 12, described above.

FIG. 6 illustrates a marker 46 used in accordance with one aspect of the present invention with a control tip 10. While control tip 12 can also be used, the function of flash hole or holes 26 is assumed by the combination of proximal tapered portion 20 of head 16 and the distal end 52 of marker 46, optionally further including a tapered countersunk port therein. In a manner similar to that described above with reference to FIG. 4, the marker 46 can be used to control puncture site 9. By moving the assembly of the control tip 10 and the marker 46 longitudinally, the distal end 52 of the marker 46 and the proximal tapered portion 20 of the head 16 can be used to throttle the flow of blood into the annular lumen 54 in a manner similar to a needle valve. That is, by drawing the head 16 closer to the puncture site 9, the flow cross-sectional area is made smaller, thereby reducing the flow of blood into the lumen 54, and pushing the assembly distally increases the flow area, increasing the flow of blood. As the proximal end 50 is not sealed with shaft 14, blood flash B can be observed out of the proximal end of the marker 46, indicating that the marker is in fluid communication with the blood vessel 5. Furthermore, as wire 28 and port 32, as described above, permit little or no blood to flow into lumen 34 of the shaft 14, the blood flash B at proximal end 50 can be a reliable indicator that the blood vessel has been accessed.

In the embodiments of FIGS. 3a–6, it is preferable that the distal end of the depth marker has significant radial or lateral clearance from the control tip shaft, so that the two elements will move laterally relative to each other near the marker's distal end, which promotes tactile feedback to the practitioner when the control tip enters the blood vessel.

FIG. 7 illustrates a side elevational view of a system in accordance with the present invention. The system generally includes a control tip 10 or 12, a pledget pusher 37, a delivery cannula 56, a pledget 90, and a proximal handle 62. As illustrated in FIG. 7, pledget 90 is positioned in a lumen 58 in delivery cannula 56 and around shaft 14 of control tip 12. Pusher 37 is also positioned in lumen 58, and has a length such that, when the pusher is in a retracted, proximal position illustrated in FIG. 7, the distal end 42, 52 of the pusher is proximal of the distal end of the delivery cannula 56. A pledget 90 is positioned in the distal portion of the lumen 58 distal of the distal end of the pusher 37 so that the pusher can push the pledget distally out of the delivery cannula. Pledget pusher 37 is structurally very similar to either pusher 36 or pusher 46, but is not attached to the control tip 10, 12 over which it longitudinally slides.

The pledget 90 according to one preferred embodiment of the invention is formed from a sheet of absorbable sponge material which has been cut into a rectangular shape and rolled to form a compact, substantially cylindrical, elongated pledget. One type of absorbable sponge material which is acceptable for use in the present invention is Gelfoam™, manufactured by the Pharmacia & Upjohn Company. Gelfoam™ is a porous, pliable, cross-linked gelatin material and is available commercially in sheet form as pre-compressed or non-compressed sponge. The material may be provided preformed as a pledget 90 or may be cut with a punch, or a stencil, or template and knife and rolled to form a pledget. Once hydrated, the pledget 90 can be easily compressed to fit into a lumen having a smaller cross sectional area than the original cross sectional area of the pledget. Additionally, the kneading of the hydrated pledget 90 during delivery encourages air trapped within the Gelfoam™ to be expelled and replaced with fluid, allowing rapid expansion upon delivery. When a pledget 90 of a pre-compressed Gelfoam™ is hydrated and kneaded (expelling air) during delivery, the pledget will have the absorption capacity to rapidly expand to many times (e.g., 3 or more times) its original dry volume upon delivery. When a pledget 90 of the non-compressed Gelfoam™ is hydrated and kneaded (expelling air) during delivery, the pledget will have the absorption capacity to rapidly expand to its original dry volume upon delivery. These properties make the Gelfoam™ sponge material particularly useful for facilitating hemostasis of puncture sites by injection.

The delivery cannula 56 includes a proximal hub 60. Hub 60 includes mating structures to mate with corresponding mating structures formed in a distal hub 76 of handle 62. By way of example and not of limitations, the mating structures of hub 60 and hub 76 can be luer fittings, screw threads, releasable bayonet fittings, and any other fitting which can releasably connect together hubs 60, 76 so that the delivery cannula 56 and the handle 62 can be moved together when the structures are mated, and the delivery cannula and handle can be separated and moved independently when the structures are released.

Pusher 37 includes a proximal hub 78 which both limits the proximal and distal movement of the pusher, and provides an enlarged section at which a practitioner can grasp the pusher if necessary. Hub 78 optionally further includes a proximal outwardly flared stop 80 which limits longitudinal motion of the pusher 37 relative to the handle 62 and other structures of the system, described in detail below. More particularly, stop 80 limits distal motion of the pusher 37, because it has an outer dimension (e.g., diameter) larger than portions of hub 76 of handle 62, and limits proximal motion because the stop is longitudinally aligned with portions of a motion limiting device 82 (described below) positioned proximal of the stop.

Handle 62 generally provides a place for a practitioner to grasp and manipulate the control tip 12, pusher 37, and delivery cannula 56 together, while also permitting the practitioner to separately move these individual components. Therefore, while a particular embodiment of a handle in accordance with the present invention is illustrated in FIG. 7, the present invention relates more generally to structures which performs these functions.

Handle 62, as illustrated in FIG. 7, includes a first side 64, a second side 66, and an open interior space 68. By providing handle 62 with an open construction, such as that illustrated in FIG. 7, a practitioner is able to access the proximal portions of pusher 36, 46 and control tip 12 in order to manipulate these elements. Each of the sides 64, 66 includes a wing 70, 72, respectively, which is optionally further provided to provide a bearing surface for a practitioner to pull the handle and any attached elements proximally.

The proximal end of the handle 62 includes an opening, slot, or the like 74 which receives a proximal motion limiting device 82 for the control tip 12. In the embodiment illustrated in FIG. 7, device 82 includes a proximal flange 84 which extends radially beyond the extent of opening 74, and therefore limits distal motion of the device 82 as it slides in the opening 74. The device 82 also includes a central cylindrical portion 86 which longitudinally slides in opening 74. A distal bumper 88 of device 82 is also radially larger than opening 74, and limits proximal motion of the device 82 relative to the handle 62. The flash tube or shaft 14 is secured to and preferably extends proximally through device 82, as illustrated in FIG. 7. Thus, the entire control tip 12 is permitted to move longitudinally over a limited range delimited by the proximal flange 84 and the distal bumper 88. Because the control tip 12 is therefore permitted to move longitudinally over only a limited range defined by device 82, and handle 62 is attached to delivery cannula 56 via hubs 60 and 76, the control tip is capable of moving longitudinally over only a limited range relative to the delivery cannula. The magnitude of range X (see FIGS. 3a, 5, and 8A) is between about 0.025 inches (0.06 cm) and about 0.25 inches (0.6 cm), preferably between about 0.1 inches (0.25 cm) and about 0.2 inches (0.51 cm), and more preferably about 0.15 inches (0.38 cm).

As will be readily appreciated by one of ordinary skill in the art, device 82 can take forms different from those illustrated in FIG. 7, while still performing the functions describe above. By way of example and not of limitation, device 82 and handle 62 can include other types of complementary surfaces, including mating threads, tabs and slots, and the like, within the scope of the present invention. Furthermore, opening 74 can be formed open on one lateral side, so that device 82 can be snapped into the handle 62 in a direction into or out of the plane of view of FIG. 7, thereby permitting assembly and disassembly of the handle with the other elements of the system. To facilitate this assembly and disassembly, it is advantageous to form at least the proximal portions of handle 62 of a resilient material which will deform to permit the device 82 to be snapped into the handle.

FIGS. 8a–8f illustrate a system as illustrated in FIG. 7 used in accordance with an exemplary embodiment of the present invention. After an endoluminal procedure which has been performed using, in part, a Seldinger technique for access to the patient's vasculature, a wire 28 is advanced into the patient's blood vessel 5 through a puncture site 9 in the vessel wall 7. A control tip 12, pusher 37, delivery cannula 56, handle 62, and pledget 90 are advanced together over the wire 28, as illustrated in FIG. 8a. According to a less preferred embodiment, the control tip is first advanced over the wire and into the blood vessel, and thereafter the delivery cannula, handle, pusher, and pledget are advanced over the control tip. As the practitioner advances the system along the wire 28, the control head 24 passes through the puncture site 9. Because the vessel wall presents more resistance to the control head than the subcutaneous tissues 3, the practitioner can feel when the control head has reached the outer portions of the puncture site 9. The practitioner then advances the control head further into the patient and into the blood vessel 5.

When the hole 26 enters the blood vessel 5, blood B flashes out the proximal end of flash tube 14, as described above, indicating to the practitioner that entry to the blood vessel has been made. Because blood may have previously been present in lumen 34 of shaft 14, and therefore potentially has already clotted or coagulated, blocking the lumen 34, it is preferable that lumen 34 be coated with a blood anticoagulant, as described above. Another tactile indication to the practitioner that entry to the blood vessel 5 has been made is provided by the distance or gap X between the proximal end of the control head 24 and the distal end of the delivery cannula 56. Because the overall flexibility of the system between the proximal end of the control head 24 and the distal end of the delivery cannula 56 is less than both the longitudinally adjacent sections of the system, the practitioner can feel that the system is more easily moved laterally when the control head 24 is in the position illustrated in FIG. 8a. Conversely, when the practitioner does not feel this reduced resistance to lateral movement of the system, the practitioner has an indication that the blood vessel 5 has not been properly accessed.

FIG. 8b illustrates a stage in the exemplary method later than that illustrated in FIG. 8a. After the practitioner has accessed the blood vessel 5 as described above, the entire system is advanced down the wire 28, as suggested by the arrow in the figure. Advancement of the system is halted when the distal end of the delivery cannula 56 engages the outer portions of the puncture site 9. As described above, as the vessel wall 7 provides more resistance to advancement of the system than does the adjacent subcutaneous tissues, the practitioner can feel when the delivery catheter has engaged the vessel wall. Verification that the delivery catheter is properly engaged against the vessel wall 7, and not merely hung up on a somewhat more resilient anatomical structure within the subcutaneous tissues, is provided by blood flash out the proximal end of the flash tube 14. At this point, the puncture site 9 is controlled by the delivery cannula 56.

FIG. 8c illustrates a stage in the exemplary method later than that illustrated in FIG. 8b. After the delivery cannula has engaged the outer surface of the puncture site 9, the device 82 (described above) is pulled proximally relative to the handle 62 while the remaining elements of the system are held stationary. The control tip 12, including the control head 24, is retracted proximally and engages the inner surface of the vessel wall at the puncture site 9. Thus, both the interior and exterior surfaces of the vessel wall 7 are engaged by portions of the system, which controls blood flow out of the puncture site. As discussed above, access to device 82 is facilitated by the open structure of handle 62, permitting a practitioner to more easily pull the device 82 proximally relative to the handle 62. Additionally, as the control head 24 is positioned distally of the pledget 90 and controls access to the blood vessel through the puncture site 9, the pledget is inhibited, and preferably prevented, from entering the blood vessel. Thus, the present invention is also advantageous because it can be used to prevent introduction of all or portions of a pledget into the bloodstream of a patient, which could otherwise initiate a clotting sequence in the blood vessel, with predictably hazardous consequences to the patient.

FIG. 8d illustrates a stage in the exemplary method later than that illustrated in FIG. 8c. The handle 62, delivery cannula 56, and control tip 12 have been retracted proximally, while holding stationary the pusher 37, such as by pulling proximally on the distal portions of bumper 88 while engaging the proximal portions of stop 80 to prevent its longitudinal motion. Proximal retraction of the delivery cannula 56 relative to the pusher 37 causes distal portions of the pledget 90 to be exposed, while at the same time the pusher does not move and is left positioned at the exterior surface of the blood vessel 5 at the puncture site 9. At the same time, proximal portions of the control head 24 are drawn through the distal portions of the pledget 90. It is preferable that the handle 62, delivery cannula 56, and control tip 12 are moved only part of the distance necessary to completely expose the pledget 90 and for stop 80 to engage portions of hub 76, as illustrated in FIG. 8d, so that the pledget can be expressed and compressed, as described below with reference to FIG. 8e.

FIG. 8e illustrates a stage in the exemplary method later than that illustrated in FIG. 8d. While holding handle 62 stationary relative to the patient, the pusher 37 is advanced distally down the control tip 12, which expels or pushes the remainder of the pledget 90 out of the lumen 58 and simultaneously compresses the pledget against the external surface of the blood vessel wall 7 at the puncture site 9. During this expulsion process, the control head 24 is positioned in the puncture site 9, and therefore at least inhibits, and preferably prevents, the pledget 90 from being pushed into the blood vessel 5. In this manner, the puncture site 9 is controlled throughout the steps of positioning the pledget 90 adjacent to the exterior of the puncture site and both inhibits bleeding and inhibits the introduction of material, including the pledget 90 as well as tissue fragments, into the blood vessel.

FIG. 8f illustrates a stage in the exemplary method later than that illustrated in FIG. 8e. The handle 62 is released from its connection with the delivery cannula 56 by releasing the connection between hub 76 and hub 60. The handle is then retracted proximally, carrying with it the control tip 12 and the pusher 37. The delivery cannula 56 is preferably held stationary in the patient during this retraction, so that the delivery catheter can hold the pledget 90 in place. As the control head 24 is pulled out of the puncture site 9, the site is compressed by the pledget 90, which inhibits bleeding and promotes closure of the puncture site. As the control tip 12 is further retracted, the control head 24 is drawn through the pledget, while the delivery cannula inhibits the pledget from following the control tip back up into the delivery cannula. The handle, pusher, and control tip are then completely removed. Then, the delivery cannula is removed, preferably slowly and with the application of localized compression to the epidermis above the puncture site, leaving the pledget 90 in place to promote healing of the puncture site 9 and inhibit blood flow from the blood vessel.

Also illustrated in FIG. 8f is an exemplary embodiment of the mating structures of hubs 60 and 76 which releasably hold together the handle 62 and the delivery cannula 56. As illustrated in FIG. 8f, hub 60 includes a mating structure 92, e.g., a tubular extension 94 including a tab 96 extending radially therefrom. Hub 76 includes an internally threaded collar 96 which receives the extension 94 therein and secures the two elements together.

FIG. 9 illustrates an exemplary embodiment of a pledget loading device 100 useful for preparing a pledget 90 and loading the pledget into a delivery cannula. As illustrated in FIG. 9, the pledget loading device 100 includes a body 102 having an interior chamber 104. A tubular receiving element 106 extends distally from the distal end of the body, and includes a lumen 116 therein communicating the interior chamber 104 with the exterior of the body. A fluid coupling 108 extends proximally from the end of the body opposite the element 106, and includes a flange, tab, or the like 112 and an internal lumen 114 which communicates the interior chamber 104 with the exterior of the body. The flange 112 is structured to releasably mate with a corresponding structure on a high pressure fluid delivery device, e.g., a syringe with a luer fitting. The body 102 also includes a stop 110 positioned in the lumen 116 which prevents a delivery cannula of a size greater than the internal dimension of the stop from entering into the chamber 104.

FIG. 10 illustrates the pledget loading device 100 with a delivery cannula 56, pusher 37, and a control tip 12 inserted into the tubular receiving element 106. As described above, stop 110 is sized so that the delivery cannula 56 is prevented from entering into the chamber 104, and preferably forms a fluid seal with the stop 110, the inner surface of the element 106, or both. The pusher 37 and the control tip 12 extend into the chamber 104. The combination of the tapered countersunk distal end 52 of the pusher and the tapered proximal portion 20 of the control head 16, 24 form a fluid control member 118 which operates in a manner similar to a needle valve. The operation of fluid control member 118 will be described in greater detail below.

In FIG. 11, a cylindrical pledget 90 has been inserted into the chamber 104. The pledget can be placed in the chamber 104 before or after the control head 16, 24 is positioned in the chamber. A source of hydration fluid, such a syringe (not illustrated), is coupled to fluid coupling 108, and hydration fluid F is injected into the chamber 104. Air in the chamber 104 is allowed to escape through fluid control member 118, while the pledget 90 is retained in the chamber and hydrated. As illustrated in FIG. 12, to assist in hydrating the pledget 90, the pusher 37, is retracted into the lumen 58 of the delivery cannula 56, in effect opening the fluid control member 118. Air and hydration fluid are then allowed to flow past the stop 110, through the lumen 58, through the lumen 39 of pusher 37, and out of the system. As illustrated in FIG. 13, the further introduction of high pressure fluid into chamber 104 forces the hydrated pledget 90 past the stop 110 and into the portion of lumen 58 not occupied by the pusher 37, while hydration fluid continues to flow out the lumen 39. In this manner, the hydrated pledget 90 is loaded into the end of the delivery cannula 56.

FIG. 14 illustrates yet another embodiment of a control head in accordance with the present invention. As illustrated in FIG. 14, a constant outer diameter guidewire 120 is slidingly received in the tapered distal portion 20 of a control tip 24. At the distalmost end of the distal portion 20, the guidewire 120 and the tapered portion 20 are nearly the same size, so that there is little or no blood flow into the interior 30 of the control head 24 past the guidewire. Such an arrangement helps assure that any blood flow into the flash tube 14 (see FIGS. 1a–1d) enters the control head 24 through the hole 26.

FIG. 15 illustrates yet another embodiment in accordance with the present invention. The proximal end of shaft 14 is fitted with a removable insertion tip 130 so that the proximal end of the shaft, with the tip 130 mounted in the shaft as illustrated in FIG. 15, can be backloaded through a pledget (not illustrated) held within a distal end of a delivery cannula (not illustrated). The insertion tip, in the embodiment illustrated in FIG. 15, includes a shank 132 and a head 134 attached to the shank. The shank has an outer dimension (e.g., diameter) sized to be received in the lumen 34 of the shaft 14, and can be large enough to form an interference or press fit with the shaft. The shank 132 and the head 134 meet at a shoulder 136 which abuts the proximalmost end of the shaft 14. The head preferably includes a pointed or otherwise tapered tip 138 which assists in moving portions of the pledget radially outward when the shaft and insertion tip 134 are pushed longitudinally through the pledget.

FIG. 16 illustrates yet another embodiment in accordance with the present invention. A stylet 150 is inserted through a control tip 10 or 12 and assists in inserting the control tip through a pledget (not illustrated) positioned inside a delivery cannula (not illustrated). The stylet 150 includes a head 152 and a shaft 154 connected to and extending from the head. The shaft 154 is sized to slide through the control tip and shaft 14. The head 152 is enlarged to facilitate pushing on the head to push the proximal end of the shaft 14 through a pledget; the shaft 154 extends from the proximal end of the shaft to assist is radially parting the material of the pledget.

FIG. 17 illustrates yet another embodiment in accordance with the present invention, in which a delivery cannula 160 includes a control tip 168 integral with the delivery cannula. The delivery cannula 160 has a tubular wall 162 which extends longitudinally between a proximal end 162 and a distal end 164, which distal end is preferably rounded to ease its insertion through subcutaneous tissues and limit trauma to the vascular wall when it is pressed against it. A lumen 166 extends through the delivery cannula 160 between the proximal end 162 and the distal end 164, and is sized in a manner similar to the other embodiments described herein to receive a pledget, pledget pusher, and/or wire.

Formed integrally with the delivery cannula 162, the control tip 168 extends longitudinally between a proximal end 170 and a distal end 172 radially offset from the center longitudinal axis of the lumen 166. The control tip 168 includes a longitudinally extending lumen 174 and a vent port or hole 176 similar to hole or holes 26. As in other embodiments described herein, the distal end 172 is preferably tapered, and preferably has an inner diameter which tapers distally, as at 178, to form a dynamic seal with a wire (not illustrated) over which the control tip 168 is inserted. As illustrated in FIG. 18, the external taper 180 of the distal end of the control tip 168 can extend proximally toward the delivery cannula 160, and the vent hole 176 is preferably formed in this tapered section. Less preferably, however, the vent hole 176 can be formed in the untapered portion 182 within the scope of the present invention.

Figure 19:
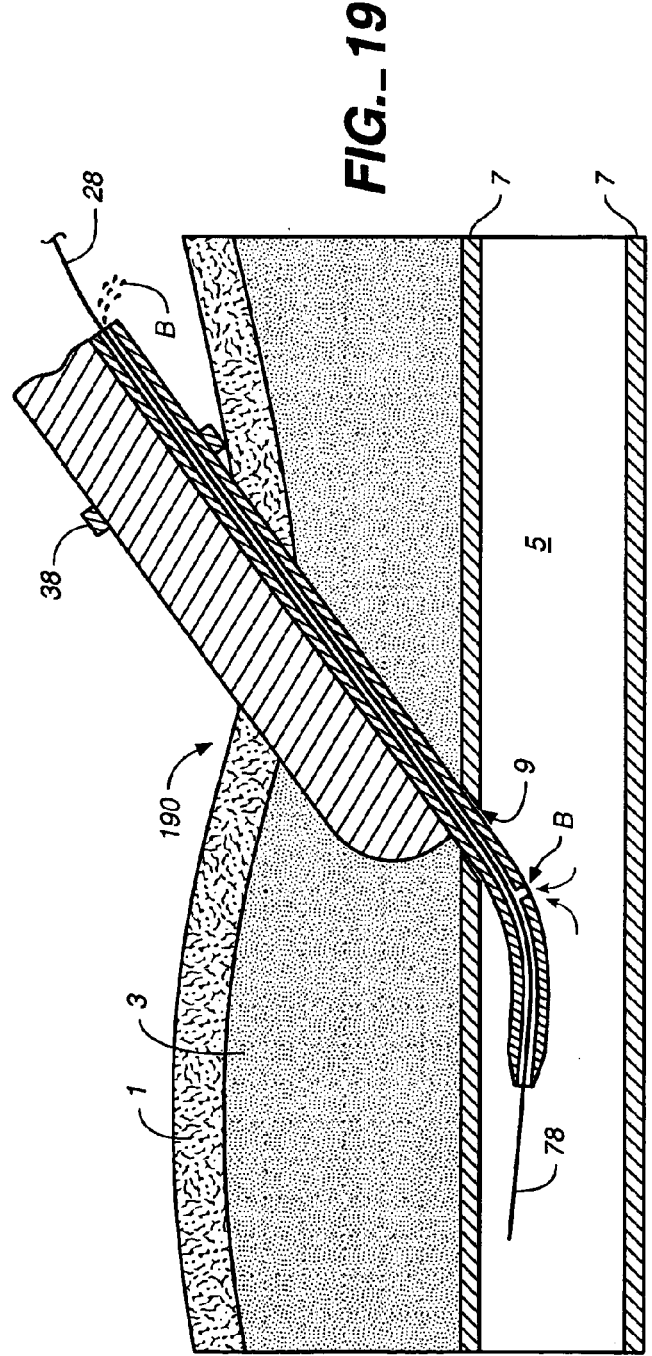
FIG. 19 diagrammatically illustrates a cross-sectional view of yet another embodiment in accordance with the present invention in one preferred use.

FIG. 19 illustrates yet another embodiment in accordance with the present invention. A depth marker 190 is similar to the delivery cannula 160 having the integral control tip 168, but does not include a lumen 166. A collar 38 is positioned on the outer surface of the depth marker, and permits the user to record the depth of the blood vessel 5 relative to the outer surface of the epidermis 1. The depth marker 190 is otherwise used in the same manner as the other embodiments of depth markers described herein.

FIG. 20 illustrates yet another embodiment in accordance with the present invention. A biaxial delivery cannula 200 includes a lumen 202 sized to receive a pledget 90 and a pledget pusher or piston 204 which extends proximally out of the delivery cannula 200. The delivery cannula 200 also includes an integral control tip 206 having a longitudinally extending through lumen 210 extending from the control head 208 proximally to the proximal end of the delivery cannula in a manner similar to other embodiments described herein. The lumen 210 is sized to slidingly receive the wire 28, and preferably forms a seal with the wire 28 as also described elsewhere herein.

The delivery cannula 200 further includes a vent lumen 212 laterally offset from the lumen 202 and the lumen 210, and preferably between the lumenae 202, 210. In a fashion similar to that previously described herein, the vent lumen 212 permits blood to flash to the proximal end of the delivery cannula 200 to give a visual indication of when control of the puncture site 9 is made and lost.

FIG. 21 illustrates yet another embodiment in accordance with the present invention. The embodiment illustrated in FIG. 21 is similar is some respects to the embodiment illustrated in FIG. 7. A delivery cannula 56, control tip 10 or 12, pledget 90, pusher 37, and wire 28 are similar or the same as described above, and are used in combination with a coaxial vent tube 220 which extends longitudinally through the pusher 37 and the pledget 90. The vent tube 220 includes a longitudinally extending lumen 222 which is sized to receive the control tip 10, 12 therein with an annular clearance to permit blood to flash proximally through the vent tube 220. Because the vent tube 220 performs the function of permitting blood flash, the shaft 14 of the control tip 10, 12 can be formed without a lumen 34, and can be dimensioned with a smaller outer diameter to increase the annular clearance between the shaft and the vent tube 220. The shaft 14 preferably maintains its relative flexibility to permit the tactile feedback previously described herein. The embodiment illustrated in FIG. 21 is used in a manner otherwise similar to those previously described herein.

FIG. 22 illustrates yet another embodiment in accordance with the present invention. As illustrated in FIG. 22, a vent tube 230 can be used with a control tip 10, 12 SO that the vent tube and control tip are advanced laterally next to each other to the puncture site 9. The vent tube 230 permits blood to flash proximally to give a visual indication of when control of the puncture site 9 is made and lost by the control head of the control tip.

FIGS. 23a and 23b illustrate a fluid handling tube 300 useful in accordance with yet another embodiment of the present invention, one particular use of which will be described in greater detail below. The tube 300 includes a cylindrical sidewall 302 extending between a proximal end 306 and a distal end 304. A hollow interior 308 is delimited by the sidewall 302. The proximal end 306 preferably includes an enlarged portion 310 which assists the tube 300 in conducting fluid therethrough. At least one, and preferably numerous fluid ports 312 are formed through the sidewall 302 adjacent to the distal end 306.

FIGS. 24a–24c illustrate several views of a handle 400 according to yet another embodiment of the present invention. Handle 400 is similar in many respects to handle 62. Handle 400 includes a top portion 402 and a bottom portion 404 which together form a generally rectangular housing. The handle 400 includes a proximal end 406 and a distal end 408. A releasable hollow locking hub 410 extends distally from the distal end 408, and is structured to releasably mate with a proximal hub of a delivery cannula, similar to cannula 56 and described in greater detail below. A longitudinally extending slot 412 is formed in each of the top 402 and bottom 404, each slot 412 including a proximal enlarged portion 414 and a proximal narrow portion 416. Adjacent to and on at least one, and preferably both sides of both narrow portions 416 are formed ramps 418 which extend outwardly from the outer surfaces of the top 402 and bottom 404 a distance sufficient to interfere with the movement of portions of a pledget pusher handle, described in greater detail below.

Also formed at the distal end of the ramps 418 are at least one, and preferable a pair of upstanding locking lips 422, one pair on the top 402 and one on the bottom 404. The lips 422 extend outwardly from the top 402 and bottom 404 a distance sufficient to enable portions of a pledget pusher handle to cam over the lips and releasably lock therewith, as described in greater detail below. The top 402 and bottom 404 can also optionally be further provided with raised ridges 420 adjacent the proximal end 406 which aid the user of the handle in manipulating it.

The handle 400 includes a proximal opening 424. According to one aspect of the present invention, the proximal opening 424 is U-shaped with an enlarged, more open upper portion 426. The enlarged portion 426 acts as a slot to permit portions of a control tip proximal hub, similar in some respects to hub 82 and described in greater detail below, to pass out of the handle 400 and permitting the handle and the control tip to move relative to each other. The proximal opening 424 also includes a lower slot 430 which extends distally into the handle 400, and a proximally extending stud 428. Lower slot 430 cooperates with a portion of a proximal handle of a control tip, and stud 428 cooperates with other portions of the proximal handle of the control tip, described in greater detail below.

FIGS. 25a–25d illustrate several views of a pledget pusher 500 according to yet another embodiment of the present invention. Pusher 500 is similar in some respects to pusher 37 described above. Pusher 500 includes a proximal end 502, a distal end 504, and a hollow tubular member 506 extending between the ends. As can be seen in the illustrations of FIGS. 25a and 25b, the distal end 504 includes an enlarged portion 508. In some aspects of the present invention, the enlarged portion 508 can have a trumpet, flared, or tulip-like shape. The enlarged portion 508, as will be described below, assists in both preparing a pledget for implantation as well as pushing the pledget during the processes of the present invention. The enlarged portion 508 is sized so that the pledget pusher 500 has little or no radial space between the enlarged portion and the inner surface of a delivery cannula, such as cannula 56, when installed therein.

The proximal end 502 of the pledget pusher 500 includes a proximal hub 514 to which are attached several additional elements. At least one, and preferably two finger engaging portions 510, 512 are cantilevered to the proximal hub 514 through attachment posts 518, 518, respectively; when both portions 510, 512 are provided, they are preferably formed on diametrically opposite lateral sides of the pusher 500. As illustrated in the drawing figures, portions of the finger engaging portions 510, 512 extend distally of the attachment posts 516, 518 and include distal latches 520, 522 which extend radially inward. The distal latches are sized and positioned so that, when the pusher 500 is positioned relative to the handle 400 as described herein, the latches cam over the ramps 418 when pushed distally, and also are sized and positioned to cam over and latch the lips 422 to releasably hold together the pusher 500 and the handle 400.

The pusher 500 also includes at least one, and preferably two proximal latches 524, 526 which extend proximally from the proximal hub 514. The latches 524, 526 extend radially inward, and are sized and positioned to engage with and releasably lock with corresponding portions on the proximal hub of a control tip, as described in greater detail below. When both latches 524, 526 are provided, they are preferably formed on diametrically opposite lateral sides of the pusher 500. While FIGS. 25a–25d illustrates portions 510, 512 being at the same circumferential position as latches 524, 526, according to other embodiments (not illustrated) these pairs of elements are at different positions. The pusher 500 also optionally further includes one or a pair of laterally extending movement guide studs 528, 530. The studs 528, 530, when provided, are attached to the proximal hub 524 and are sized to loosely engage the inner surfaces of the handle 400 to assist in the pusher 500 to better track as it moves longitudinally.

FIGS. 26a–26c illustrate partial cross-sectional, perspective views of a pledget hydration and loading device 600 used to both hydrate a pledget 90 and load the hydrated pledget into a delivery cannula 56 in accordance with the present invention. Device 600 is similar in function to device 100, described above. Device 600 preferably includes the fluid handling tube 300 mounted therein, with the distal end 304 extending around the control tip 24 and the hole 26. In this position, the fluid handling tube 300 inhibits, and preferably prevents, hydration fluid from entering the flashback lumen of the control tip through the hole 26. As will be readily appreciated by one of skill in the art, the holes 312 are provided so that any hydration fluid which flows through the interior of the tube 300 can flow through the holes 312 and around the outside of the tube to hydrate and move the pledget 90. In the stage of hydration illustrated in FIG. 26a, the enlarged portion 508 is positioned at least at the distal end of the delivery cannula 56, and preferably distal thereto. The enlarged portion 508 thus inhibits, and preferably prevents, portions of the pledget 90 from getting behind the distal end 504 of the pledget pusher 500 when the pledget is loaded into the delivery cannula 56. By inhibiting or preventing portions of the pledget from getting behind the distal end of the pledget pusher 500, delivery of the pledget to the patient, as described above, is facilitated, and assists in preventing the pledget from being snagged on the pledget pusher.

FIG. 26b illustrates a stage in a process of hydration and loading of the pledget 90 in the pusher 500 later than that illustrated in FIG. 26a. Hydration fluid from source 602, such as a syringe, flows through the holes 312, around the outside of the tube 300, and pushes the pledget 90 into the lumen of the delivery cannula 56. FIG. 26c illustrates a stage in a process of hydration and loading of the pledget 90 in the pusher 500 later than that illustrated in FIG. 26b. Hydration fluid has pushed the pledget 90 entirely into the delivery cannula 56, with the enlarged portion 508 of the pusher 500 proximal of the pledget.

FIGS. 27a–27c illustrate perspective views, with portions broken away to aid in an understanding of the invention, of proximal portions of the pusher 300, handle 400, and a proximal hub 700 of a control tip 14 assembled together in accordance with the present invention. The distal portions of the control tip are similar to the distal portions of control tip 14, described above.

In FIG. 27a, the pledget pusher 500 is positioned adjacent to the distal hub 410 of the handle 400. The proximal hub 700 includes at least one, and preferably a pair of laterally extending wings 702, 704, which assist the user of the devices in manipulating the control tip 14. A proximal cylinder 706 extends distally from the wings 702, 702, and extends through the proximal opening 424 of the handle 400. The enlarged portion 426 acts as an upper open end 426 and the lower slot 430 are also illustrated in FIG. 27a. A first laterally extending key 708 is formed at a distal end of the cylinder 706, and a second laterally extending flange 710 is formed at least partially along the length of the cylinder and diametrically opposite the first key 708. Because of the perspective at which FIG. 27a is illustrated, the flange 710 is behind the cylinder 706.

A distal cylinder 716 extends distally from the proximal cylinder 706, and preferably has a smaller outer diameter. At least one, and preferably a pair of ramp latches 712, 714 extend laterally from the exterior surface of the cylinder 716, with the higher portions of the ramps being at the ramps' proximal ends. The ramp latches 712, 714 are sized and positioned so that when the pledget pusher 500 is moved proximally, the proximal latches 524, 526 cam over the top surfaces of the ramp latches and releasably lock to the proximal faces of the ramp latches. This locked position is illustrated in FIG. 27b.

The first key 708 and the second flange 710 are diametrically oppositely arranged, and the ramp latches 712, 714 are also diametrically oppositely arranged. Another aspect of the present invention is that the key 708/flange 710 pair are offset along the circumferences of the cylinders 706, 716 from the ramp latches 714/712 pair. While in the embodiment illustrated in FIGS. 27a–27c, this offset is approximately the maximum 90 degrees, this angular offset can, within the scope of the present invention, be less than 90 degrees. This angular offset is useful in the present invention to restrict the relative motions of several of the elements described herein. More specifically, rotational motion of the control tip 14 and its proximal hub 700 relative to the handle 400 and the pledget pusher 500 unlocks the pusher from the control tip, and aligns the key 708 with the opening 424, and aligns the flange 710 with the slot 430, thus permitting the proximal hub 700 to be moved proximally relative to the handle 400.

FIG. 27b illustrates the pledget pusher 500 after having been moved proximally so that the proximal latches 524, 526 have cammed over the ramp latches 712, 714, securing the pusher to the control tip 14. Notable is that the finger engaging portions 510, 512 of the pusher 500 extend through the slots 412 of the handle 400, and therefore the pusher cannot rotate relative to the handle. In the orientation illustrated in FIG. 27b, only the proximal hub 700 can rotate relative to the handle 400, and that relative rotation is also restricted, as described below.

FIG. 27c illustrates relative positions of the proximal hub 700, handle 400, and pusher 500 after the hub 700 has been rotated clockwise (as seen from the proximal end of the assembly) and retracted proximally. In this position, the ramp latches 712, 714 have been rotated away from the proximal latches 520, 522, which permits the proximal hub 700 to move independently off the pledget pusher. This rotation of the proximal hub 700 is also relative to the handle 400, and results in the alignment of the key 708 with the open upper end 426, and the alignment of the flange 710 with the slot 430. The proximal hub 700 includes a set of structures on distally directed portions of the wings 702, 704, which cooperate with the stud 428 on the proximal end of the handle to restrict the motion of the proximal hub 700 relative to the handle 400 to a single direction of rotation. In the embodiment illustrated in FIG. 27c, a first notch 720 is separated from an elongated second notch 722 by a cam 724. The first notch 720 is in part defined by a face 728, and the second notch is in part defined by a face 726. As can be readily appreciated from FIG. 27c, the second notch 722 is axially aligned with the stud 428 (which, because of the perspective of the illustration, is obscured) when the flange 710 is in the slot 430. When the proximal hub 700 is in the positions illustrated in FIGS. 27a and 27b, the stud 428 is positioned between the cam 724 and the face 720, i.e., in the first notch 720. In the orientations of FIGS. 27a and 27b, the face 728 prevents the proximal hub 700 from being rotated in the direction of arrow 732, while the stud 428 can, with the exertion of additional force, move past the cam 724 in the direction of arrow 730 and into the second notch 722. The face 726, however, restricts further rotational motion of the proximal hub 700 relative to the handle 400 because the stud hits the face 726. The relative movement of the proximal hub 700 and the handle 400 are thus restricted by the stud 428, notches 720, 722, key 708, flange 710, open end 426, and slot 430.

FIGS. 28a–28c illustrate a collar 38 positioned on the outer surface of the delivery cannula 56, as described above, in combination with several alternative embodiments of the present invention. The collar 38 assists the user of the devices of the present invention in correctly positioning the control tip in the blood vessel of a patient, as discussed above. Additionally, it is advantageous for the length of the control head 24 to be equal or larger than the insertable length of the delivery cannula 56. By sizing the control head 24 in this manner, the user can achieve blood flow control at the puncture site much faster before the distal end of the delivery cannula reaches the puncture site.

FIGS. 29a–29c illustrate several steps of methods in accordance with the present invention, utilizing the handle 400, pledget pusher 500, and control tip proximal hub 700 described above. The steps illustrated in FIGS. 29a–29c correspond to the steps illustrated in FIGS. 8c, 8d/8e, and 8f, respectively. In the step illustrated in FIG. 29a, the proximal hub 700 has been rotated and released from both the handle 400 and the pledget pusher 500, while blood B drips out the proximal end of the control tip 14, and the enlarged portion of the control head 24 is positioned at the puncture site to achieve blood flow control. In FIG. 29b, the finger engaging portions 510, 512 are urged distally, driving the pledget 90 out of the distal end of the delivery cannula 56. During this pushing step, the ramps 418 interfere slightly with the distal motion of the portions 510, 512, which provides tactile feedback to the user that the end of the push is approaching. At the end of the distal travel of the pledget pusher 500 relative to the handle 400, the distal latches 520, 522 cam over and latch with the lips 422, holding the pusher, handle, and delivery cannula 56 together. The user can then release the pledget pusher, as in FIG. 29c, from the handle by pressing on the cantilevered proximal portions of the finger engaging portions 510, 512, and can retract the pledget pusher, while the enlarged portion of the control head 24 remains in the puncture site to control blood flow. The delivery cannula 56 can then be released from the handle 400, and the pledget pusher and control tip withdrawn from the patient.

FIGS. 30–32 illustrate several embodiments of devices in accordance with the present invention. Three exemplary devices are illustrated in FIGS. 30–32 useful to overcome the limitations relating to blood dripping from the proximal end of the flash tube 14.

FIG. 30 illustrates an elevational view of a tube 800 having a distal inside diameter 806 equal to or larger than the outside diameter of the proximal flash tube 14. Preferably, the tube 800 is placed over the proximal flash tube 14. According to a preferred embodiment, the tube 800 is formed of a material which exhibits very high surface tension with blood, e.g., PTFE, and extends proximally of the proximal end of the flash tube 0.5 cm to 5.0 cm, and more preferably 1.5 cm to 2.5 cm. In a more preferred embodiment, the flash tube 14 has an ID ("inner diameter") of 0.040", the guidewire 28 (see FIG. 2) has an OD ("outer diameter") of 0.025", and the Teflon tube has an ID of 0.060".

The tube 800 is preferably extremely hydrophobic and has a very high surface tension. Any blood exiting the tube 800 at proximal end 802 immediately forms a drop and falls free prior to reaching the handle; as the device is typically used at an angle not exceeding about 60 deg from horizontal, the drop can form and fall. A short, less hydrophobic proximal flash tube "wets" out and shunts blood directly into or onto the adjacent fittings and handle. Further, the tube 800 has a larger ID at distal end 804 than the proximal flash tube and extends proximally of it, allowing the tube to act as a reservoir to slowly accumulate any tip or tract oozing prior to the bleed-back hole 26 entering the blood vessel lumen. In this way, oozing that would otherwise be observed exiting the proximal flash tube 14, and possibly be misinterpreted, is contained within the tube 800, allowing sufficient time to advance the system until the bleed-back hole 26 enters the blood vessel lumen. When the bleed-back hole enters the blood vessel lumen, the volume of blood exiting the proximal flash tube 14 increases dramatically and immediately (i.e. 1 second) fills the tube 800 and begins dripping free. The coaxial orientation of the tube 800 relative to the guidewire 28 ensures consistent interpretation of the bleed-back regardless of the radial alignment of the device with respect to the tissue tract.

FIG. 31 illustrates a cone 810 having a proximal inside diameter 812 sized as described above for ID 806. The large diameter end 814 of the cone 810 is axially separated from the handle, e.g. 400, or is larger in diameter than any luer or handle structure adjacent to it, or both. According to a preferred embodiment, the cone extends proximally of the proximal end of the flash tube 14 0.5 cm to 5.0 cm, and more preferably 1.5 cm to 2.5 cm. In a more preferred embodiment, the flash tube 14 has an ID of 0.040", the guidewire 28 has an OD of 0.025", and the cone has an ID of 0.060".

The large proximal end 814 of the cone further provides a definitive point from which the drop can fall if it should get that far along the exterior of the cone 810, providing additional certainty that the drop does not reach the luer or handle. As with the tube 800, the cone 810 can act as a reservoir for blood.

FIG. 32 illustrates a cone 820 and elbow 824 having a distal inside diameter 822 as described above for diameters 806 and 812. The cone 820 includes a port 826, preferably in the area of the elbow 824, sized to permit the guidewire 28 to pass therethrough. Thus, the material of the cone 820 at the port 826 acts to restrict or eliminate the flow of blood out the port 826, causing the blood to flow out the proximal end 828 of the cone. The elbow 824 is generally tubular and extends at an angle preferably greater than about 30 deg, or may alternatively extend in a "dog-leg" or otherwise offset fashion allowing the cone to extend laterally from the proximal end of the flash tube 14. As with the tube 800 and the cone 810, the cone 820 is formed of a material which is extremely hydrophobic and has a very high surface tension, and can act as a blood reservoir. Additionally, if the elbow port 826 is sized relative to the guidewire 28 to only partially restrict blood flow through it, the port will serve to vent "ooze" out of the cone, reducing the burden on the "reservoir". The radial offset of the cone from the guidewire, rather than the coaxial orientation discussed previously, acts to further highlight the bleed back, although it may be interpreted differently depending upon the radial alignment of the device with respect to the guidewire axis.

For all of the embodiments of the control tip herein, the outer diameter of the central portion is between about 5 French and about 9 French, preferably between about 6 French and about 7 French. The length of the control head, between the distalmost end and the proximal end of the proximal tapered portion, is between about 1.5 inches (3.8 cm) and about 3 inches (7.6 cm), preferably between about 1.5 inches and about 2 inches (6.4 cm), and more preferably about 1.875 inches (4.8 cm). Control heads of these dimensions are well suited for controlling puncture sites as described herein, particularly puncture sites used during Seldinger-type vascular access.

The transverse cross sectional profile of all of the foregoing structures can be any desired shape, including square, oval, triangular, and preferably circular. The materials out of which the control tip, pledget pusher, and delivery cannula are constructed are preferably selected to be relatively rigid and biocompatible, and more preferably are biocompatible polymers, biocompatible metals and metal alloys, and combinations thereof.

While the invention has been described in detail with reference to preferred embodiments thereof, it will be apparent to one skilled in the art that various changes can be made, and equivalents employed, without departing from the scope of the invention. All of the aforementioned documents are incorporated by reference in each of their entireties herein.

What is claimed is:

1. An apparatus to hydrate and deliver a pledget substantially adjacent to a blood vessel puncture site, comprising:
   a control tip including:
      a vent tube having a tubular shaft with a proximal end having a hub, a distal end, and a lumen extending between the proximal end and the distal end;
      a control head on the distal end of the vent tube, the control head including an externally tapered proximal end portion, a distal end portion having a distal port, and a central portion between the proximal end portion and the distal end portion, the control head including a lumen extending between the distal port to the vent tube shaft lumen;
   a pledget pusher positioned around the vent tube shaft, the pledget pusher including a proximal end having a hub, a distal end having an enlarged portion, and a lumen extending longitudinally between the pledget pusher proximal end and the pledget pusher distal end, the inner diameter of the pledget pusher lumen being larger than the outer diameter of the vent tube;
   a delivery cannula positioned around the pledget pusher, the delivery cannula including a tubular shaft having a proximal end having a hub, a distal end, and a lumen extending longitudinally between the delivery cannula proximal end and the delivery cannula distal end, the inner diameter of the delivery cannula lumen being larger than the outer diameter of the pledget pusher; and
   a pledget hydrating device having a fluid handling tube to receive the control head, the fluid handling tube including:
      a first end, a second end, and a lumen extending between said first end and said second end;
      at least one fluid port located at said first end; and
      an enlarged portion at said first end having a larger diameter than said fluid handling tube lumen,
      wherein said fluid handling tube lumen extends over said distal port.

2. The apparatus of claim 1 wherein the control head extends distally from the delivery cannula distal end, the delivery cannula distal end extends distally of the pledget pusher distal end.

3. The apparatus of claim 1 further comprising a wire extending through the vent tube lumen, the wire having an outer diameter less than the vent tube lumen inner diameter.

4. The apparatus of claim 1 further comprising a handle having a top portion having a first opening, said top portion coupled to a bottom portion having a second opening, a proximal end and a distal end, the handle and said control tip hub together further comprising a motion limiting device, portions of the motion limiting device being formed on the control tip hub, and portions of the motion limiting device being formed on the handle distal end, the motion limiting device limiting longitudinal motion of the pledget pusher relative to the handle over a distance X.

5. The apparatus of claim 4 wherein the motion limiting device on the handle distal end comprises at least one releaseable locking ramp extending outwardly from said top portion, said at least one releaseable locking ramps located at the handle distal end.

6. The apparatus of claim 4 wherein said at least one releaseable locking ramp provides tactile feedback to a user to inform the user that the pledget pusher distal end is near the delivery cannula distal end.

7. The apparatus of claim 6 wherein said pledget pusher hub further comprises a pledget pusher handle extending outwardly from said first and second openings, at least one distal latch extending radially inward from said pledget pusher handle to releasably lock with said at least one releaseable locking ramp, at least one proximal latch extending radially inward from the pledget pusher hub to releasably lock with a latch on said control tip hub, and a first guide stud and a second guide stud opposite said first guide stud to engage an inner surface of said handle.

8. The apparatus of claim 6 wherein the pledget pusher is slidable in the delivery cannula between a distal position with the pledget pusher handle engaging the at least one releaseable locking ramps, and a proximal position with the pledget pusher proximal latch engaging the latch on said control tip hub.

9. The apparatus of claim 4 further comprising a releasable locking hub at the handle distal end to mate with the delivery cannula hub.

10. The apparatus of claim 1 further comprising a hydrating device comprising a proximal end, a distal end, an interior chamber, a tubular extension extending from the distal end, a stop adjacent the tubular extension, and a proximal opening, the tubular extension sized to receive the delivery cannula therein, the stop sized and configured to prevent the delivery cannula from entering the interior chamber and sized and configured to permit the pledget pusher and control head to pass into the interior chamber.

11. The apparatus of claim 10 wherein said fluid handling tube is sized to fit within the interior chamber with the enlarged portion adjacent the pledget hydrating device proximal end.

12. The apparatus of claim 1 wherein the delivery cannula further comprises a means for marking.

13. The apparatus of claim 12 wherein the means for marking comprises a collar.

14. The apparatus of claim 1 wherein the pledget pusher enlarged portion has a diameter substantially similar to the inner diameter of the delivery cannula lumen such that there is no space between the enlarged portion and the inner diameter of the delivery cannula lumen.

15. The apparatus of claim 1 further comprising a flash tube at said control tip hub.

16. The apparatus of claim 15 comprising a blood flow tube attached over said flash tube, said blood flow tube having a larger internal diameter than said flash tube.

17. The apparatus of claim 16 wherein said blood flow tube further comprises a blood reservoir.

18. The apparatus of claim 16 wherein said blood flow tube is a cone.

19. The apparatus of claim 16 wherein said blood flow tube is hydrophobic and has a high surface tension to inhibit shunting of a blood flow out of said blood flow tube.

20. The apparatus of claim 16 wherein said blood flow tube is angled at about 60 degrees from the horizontal.

21. A method for hydrating a pledget in an hydrating device and positioning the pledget adjacent to the exterior surface of a blood vessel puncture site, comprising:

hydrating the pledget with a fluid from a fluid source;

retracting a pledget pusher in a delivery cannula to a proximal position;

pushing said pledget into said delivery cannula and adjacent said pledget pusher;

removing said hydrating device;

advancing a control head of a control tip through the puncture site and at least partially into the blood vessel, the control tip including a proximal portion extending out of the puncture site and out of the patient;

advancing an assembly over the control tip proximal portion and adjacent to an exterior surface of the blood vessel, the assembly including the delivery cannula, the pledget pusher in the delivery cannula, and the pledget in the delivery cannula;

proximally retracting the control head; and expelling the pledget from the delivery cannula.

22. The method of claim 21 comprising positioning the control head in a fluid handling tube in the hydrating device prior to hydrating the pledget.

23. The method of claim 21 wherein retracting the pledget pusher further comprises mating a pledget pusher proximal latch with a control tip latch on a proximal end of the control tip.

24. The method of claim 21 wherein said fluid source is a syringe.

25. The method of claim 21 wherein expelling the pledget further comprises releasing said pledget pusher proximal latch from said control tip latch.

26. A method in accordance with claim 21, wherein advancing the control head and advancing the assembly are performed simultaneously.

27. A method in accordance with claim 21, wherein advancing the control head is performed before the step of advancing the assembly.

28. A method in accordance with claim 21, further comprising proximally retracting the delivery cannula and the control tip relative to the puncture site and relative to the pledget pusher.

29. A method in accordance with claim 26, further comprising proximally retracting the control tip relative to the puncture site and relative to the pledget pusher.

30. A method in accordance with claim 21, wherein expelling further comprises the step of distally advancing the pledget pusher to push the pledget out of the delivery catheter.

31. A method in accordance with claim 30, further comprising proximally retracting the control head and the pledget pusher relative to the delivery cannula, the control head being retracted through the pledget, the delivery cannula distal end engaging the pledget.

32. A method in accordance with claim 31, wherein the expelling step further comprises the step of distally advancing the pledget pusher to compress the pledget.

33. A method in accordance with claim 21, wherein the step of advancing the control tip and the step of advancing the assembly are performed simultaneously.

* * * * *